United States Patent [19]

Flynn et al.

[11] Patent Number: 5,366,973
[45] Date of Patent: Nov. 22, 1994

[54] MERCAPTOACETYLAMIDO PYRIDAZO[1,2]PYRIDAZINE, PYRAZOLO[1,2]PYRIDAZINE PYRAZOLO[1,2]PYRIDAZINE, PYRIDAZOL[1,2-A][1,2]DIAZEPINE AND PYRAZOLOL[1,2-A][1,2]DIAZEPINE

[75] Inventors: Gary A. Flynn, Cincinnati, Ohio; Patrick W. Shum, West Chester, Ohio

[73] Assignee: Merrell Dow Pharmaceuticals Inc., Cincinnati, Ohio

[21] Appl. No.: 146,857

[22] Filed: Nov. 3, 1993

Related U.S. Application Data

[63] Continuation-in-part of Ser. No. 40,003, Apr. 9, 1993, abandoned, which is a continuation-in-part of Ser. No. 884,963, May 15, 1992, abandoned.

[51] Int. Cl.$^5$ .................. C07D 487/04; A61K 31/50; A61K 31/415
[52] U.S. Cl. .................................. 514/221; 514/405; 514/248; 541/235; 548/363.1; 540/500
[58] Field of Search .................. 514/405, 248, 221; 544/235; 548/363.1; 540/500

[56] References Cited

U.S. PATENT DOCUMENTS

| | | | |
|---|---|---|---|
| 3,334,091 | 7/1967 | Houlihan | 260/243 |
| 3,334,095 | 8/1967 | Houluhan | 260/244 |
| 4,080,449 | 3/1978 | Croisier et al. | 424/244 |
| 4,320,057 | 3/1982 | Freed et al. | 260/239.3 |
| 4,391,752 | 7/1983 | Crossley | 260/239.3 |
| 4,399,136 | 8/1983 | Hassell et al. | 424/250 |
| 4,415,496 | 11/1983 | Harris et al. | 260/239.3 |
| 4,487,929 | 12/1984 | Hassell et al. | 544/224 |
| 4,512,924 | 4/1985 | Attwood et al. | 260/243.3 |
| 4,584,294 | 4/1986 | Ruyle | 514/214 |
| 4,658,024 | 4/1987 | Attwood et al. | 540/500 |
| 4,692,438 | 9/1987 | Hassall et al. | 514/183 |
| 4,716,232 | 12/1987 | Ternansky | 548/112 |
| 4,734,504 | 3/1988 | Holmes | 548/364 |
| 4,734,505 | 3/1988 | Holmes | 548/364 |
| 4,762,924 | 8/1988 | Hassall et al. | 540/501 |
| 4,772,701 | 9/1988 | Attwood et al. | 514/235 |
| 4,782,149 | 11/1988 | Lawton et al. | 540/500 |
| 4,785,093 | 11/1988 | Hassell et al. | 540/460 |
| 4,808,713 | 2/1989 | Attwood et al. | 540/487 |
| 4,824,832 | 4/1989 | Flynn et al. | 514/214 |
| 4,826,980 | 5/1989 | Hassell et al. | 544/224 |
| 4,973,585 | 11/1990 | Flynn et al. | 514/214 |
| 5,208,230 | 5/1993 | Flynn et al. | 514/214 |

FOREIGN PATENT DOCUMENTS

| | | |
|---|---|---|
| 0128728 | 12/1984 | European Pat. Off. . |
| 0249223 | 12/1987 | European Pat. Off. . |
| 0249224 | 12/1987 | European Pat. Off. . |
| 0322914 | 12/1988 | European Pat. Off. . |
| 0481522 | 4/1992 | European Pat. Off. . |
| 0492369 | 7/1992 | European Pat. Off. . |
| 0533084 | 9/1992 | European Pat. Off. . |
| 91/08195 | 6/1991 | WIPO . |
| 91/09840 | 7/1991 | WIPO . |
| 93/02099 | 2/1993 | WIPO . |

OTHER PUBLICATIONS

Fournie–Zaluski, Marie–Claude et al., *J. Med. Chem.*, 1992 vol. 35, pp. 2473–2481.
Fournie–Zaluski, Marie–Claude et al., *J. Med. Chem.*, 1992 vol. 35, pp. 1259–1266.
French, John F., *Jour. of Pharm and Exper. Therapeutics*, vol. 268, No. 1, pp. 180–186.
W. H. Parsons et al. *Biochemical and Biophysical Research Communications* vol. 117, No. 1, 1993 (Nov. 30, 1983).

(List continued on next page.)

*Primary Examiner*—John M. Ford
*Attorney, Agent, or Firm*—Charlotte L. Barney

[57] ABSTRACT

The present invention relates to certain novel mercaptoacetylamido pyridazo[1,2]pyridazine, pyrazolo[1,2-]pyridazine, pyridazo[1,2-*a*][1,2]diazepine and pyrazolo[1,2-*a*][1,2]diazepine derivatives useful as inhibitors of enkephalinase and of ACE.

31 Claims, No Drawings

OTHER PUBLICATIONS

Burkholder, et al. *Bioorganic and Medical Chem. Letters*, vol. 3, No. 2, pp. 231–234, 1993.

Flynn et al., *J. Med. Chem.* 1993, 36 2420–2423.

Flynn, et al., J. Am Chem. Soc. 109, 7914 (1987).

Flynn, et al., Peptide Chemistry (1987); T. Shiba & Sakakibara (ed.), Protein Research Foundation, Osaka (1988).

Flynn, et al., Tetrahedron Letters, vol. 31, (6), 815–88 (1990).

Attwood, et al., J. Chem. Soc. Perkin Trans. I, pp. 1011–1019 (1986).

Natoff, et al., Drugs of the Future, vol. 12 (5): 475–483 (1987).

Journal of Am. Coll. of Card. vol. 17, No. 6, pp. 137B–142B (May 1991).

Supplement I Cir. vol. 86(4) pp. 1-220(0873) (Oct. 1992).

J. Med. Chem. (1992), 35, 823–832, Timothy D. Ocain et al.

Bioorganic and Medical Chem. Letters vol. 1, 309, (1991).

MERCAPTOACETYLAMIDO PYRIDAZO [1,2]PYRIDAZINE, PYRAZOLO[1,2]PYRIDAZINE PYRAZOLO[1,2]PYRIDAZINE, PYRIDAZOL[1,2-A][1,2]DIAZEPINE AND PYRAZOLOL[1,2-A][1,2]DIAZEPINE

This is a continuation-in-part application of Ser. No. 08/040,003, filed Apr. 9, 1993, which is a continuation in part application of Ser. No. 07/884,963, filed May 15, 1992, both now abandoned.

BACKGROUND OF THE INVENTION

Enkephalinase or, more specifically, endopeptidase-24.11, is a mammalian ectoenzyme which is involved in the metabolic degradation of certain circulating regulatory peptides. This enzyme, which is a $Zn^{+2}$-metallopeptidase, exerts its effect by cleaving the extracellular peptides at the amino group of hydrophobic residues and thus inactivates the peptides as regulatory messengers.

Enkephalinase is involved in the metabolic degradation of a variety of circulating regulatory peptides including endorphins, such as $\beta$-endorphin and the enkephalins, atrial natriuretic peptide (ANP), and other circulating regulatory peptides.

Endorphins are naturally-occurring polypeptides which bind to opiate receptors in various areas of the brain and thereby provide an analgesic effect by raising the pain threshold. Endorphins occur in various forms including $\alpha$-endorphin, $\beta$-endorphin, $\gamma$-endorphin as well as the enkephalins. The enkephalins, i.e., Met-enkephalin and Leu-enkephalin, are pentapeptides which occur in nerve endings of brain tissue, spinal cord and the gastrointestinal tract. Like the other endorphins, the enkephalins provide an analgesic effect by binding to the opiate receptors in the brain. By inhibiting enkephalinase, the metabolic degradation of the naturally-occurring endorphins and enkephalins are inhibited, thereby providing a potent endorphin- or enkephalin-mediated analgesic effect. Inhibition of enkephalinase would therefore be useful in a patient suffering from acute or chronic pain. Inhibition of enkephalinase would also be useful in providing an antidepressant effect and in providing a reduction in severity of withdrawal symptoms associated with termination of opiate or morphine administration. In addition, inhibition of enkephalinase would also be useful in the treatment of irritable bowel syndrome.

ANP refers to a family of naturally-occurring peptides which are involved in the homeostatic regulation of blood pressure, as well as sodium and water levels. ANP have been found to vary in length from about 21 to about 126 amino acids with a common structural feature being one or more disulfide-looped sequences of 17 amino acids with various amino- and carboxy-terminal sequences attached to the cystine moiety. ANP have been found to bind to specific binding sites in various tissues including kidney, adrenal, aorta, and vascular smooth muscle with affinities ranging from about 50 pico-molar (pM) to about 500 nano-molar (nM) [Needleman, Hypertension 7, 469 (1985)]. In addition, it is believed that ANP binds to specific receptors in the brain and possibly serves as a neuromodulator as well as a conventional peripheral hormone.

The biological properties of ANP involve potent diuretic/natriuretic and vasodilatory/hypotensive effects as well as an inhibitory effect on renin and aldosterone secretion [deBold, Science 230, 767 (1985)]. By inhibiting enkephalinase, the metabolic degradation of the naturally-occurring ANP are inhibited, thereby providing a potent ANP-mediated diuretic, natriuretic, hypotensive, hypoaldosteronemic effects. Inhibition of enkephalinase would therefore be useful in a patient suffering from disease states characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure.

In addition, the compounds of the present invention are inhibitors of Angiotensin-Converting Enzyme (ACE). ACE is a peptidyl dipeptidase which catalyzes the conversion of angiotensin I to angiotensin II. Angiotensin II is a vasoconstrictor which also stimulates aldosterone secretion by the adrenal cortex. Inhibition of ACE would therefore be useful in a patient suffering from disease states such as hypertension and congestive heart failure [See William W. Douglas, "Polypeptides—Angiotensin, Plasma Kinins, and Others", Chapter 27, in GOODMAN AND GILLMAN'S THE PHARMACOLOGICAL BASIS OF THERAPEUTICS, 7th edition, 1985, pp. 652-3, MacMillan Publishing Co., New York, N.Y.]. In addition, it has been discovered that ACE inhibitors are useful in treating cognitive disorders [German Application No. 3901-291-A, published Aug. 3, 1989].

Bradykinin refers to a naturally-occurring peptide which is a very powerful vasodilator and causes increased capillary permeability. By inhibiting enkephalinase and ACE, the metabolic degradation of bradykinin is inhibited, thereby providing increased levels of bradykinin in the circulation.

In addition, the compounds of the present invention are useful as inhibitors of smooth cell proliferation. Smooth muscle cell proliferation in the intima of muscular arteries is a primary cause of vascular stenosis in arteriosclerosis, after vascular surgery, and after coronary angioplasy. Several animal studies have indicated the renin-angiotensin system plays an important role in this vascular response to injury. Chronic treatment with angiotensin converting enzyme (ACE) inhibitors reduced myointimal thickening following balloon injury in rat carotid artery or aorta. Powell, J. S., Muller, R. K. M. and Baumgartner, H. R.; Suppression of the vascular response to injury: The role of angiotensin-converting enzyme inhibitors. J. Am. Coll. Cardiol. 17:137B–42B, 1991. More recently, atrial natriuretic peptide (ANP) has been found to decrease myointimal proliferation. ANP is rapidly metabolized by receptor mediated clearance and by neutral endopeptidase (NEP). Inhibition of NEP significantly reduces proliferation in the balloon-injured rabbit vasculature. Davis, H. R., McGregor, D.C., Hoos, L., Mullins, D. E. and Sybertz, E. J.: Atrial naturiuretic factor and the neutral endopeptidase inhibitor SCH42495 prevent myointimal proliferation after vascular injury. Circ. 86:I-220, 1992. These studies imply that a dual inhibitor of ACE and NEP should be therapeutically useful in the treatment of conditions which require inhibition of smooth cell proliferation. Davis and Sybertz, European Patent Application 533084-A1, Mar. 24, 1993.

SUMMARY OF THE INVENTION

The present invention provides novel compounds of the Formula (I)

wherein

B represents a methylene, ethylene or vinylene group;

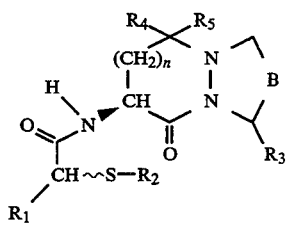

$R_1$ represents a hydrogen, $C_1$–$C_8$ alkyl, —CH$_2$OCH$_2$CH$_2$OCH$_3$ or an Ar—Y— group;

$R_2$ represents a hydrogen, acetyl, —CH$_2$O—C(O)C(CH$_3$)$_3$ or benzoyl;

$R_3$ represents a carboxyl, alkoxycarbonyl or Ar—Y—O carbonyl group;

$R_4$ and $R_5$ each represent a hydrogen atom or $R_4$ and $R_5$ together represent an oxo group;

n stands for zero, 1 or 2, and pharmaceutically acceptable salts and individual optical isomers thereof.

The present invention further provides a method of inhibiting enkephalinase in a patient in need thereof comprising administering to said patient an effective enkephalinase inhibitory amount of a compound of Formula (I). The present invention also provides a method of inhibiting ACE in a patient in need thereof comprising administering to said patient an effective ACE inhibitory amount of a compound of Formula (I).

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

As used herein, the term "$C_1$–$C_8$ alkyl" refers to saturated straight or branched chain hydrocarbyl radicals of one to eight carbon atoms, including methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein, an alkoxy group and the alkoxy moiety of an alkoxycarbonyl group can be straight or branched chain and contain from i to 8 carbon atoms, preferably from 1 to 4, carbon atoms. Specific examples of alkoxycarbonyl groups are methoxycarbonyl, ethoxycarbonyl, t-butyoxycarbonyl and the like. Specific examples of alkoxy groups are methoxy, ethoxy, t-butoxy and the like.

As used herein, the term "AR—Y—" refers to a radical wherein Ar is an aryl group and Y is a $C_0$–$C_4$ alkyl. The term "Ar" refers to a phenyl or naphthyl group unsubstituted or substituted with from one to three substituents selected from the group consisting of methylenedioxy, hydroxy, $C_1$–$C_4$ alkoxy, amino, nitro, fluoro and chloro. The term "$C_0$–$C_4$ alkyl" refers to a saturated straight or branched chain hydrocarbyl radical of zero to four carbon atoms and includes a bond, methyl, ethyl, propyl, isopropyl, n-butyl, isobutyl, tertiary butyl and the like. Specifically included within the scope of the term "Ar—Y—" are phenyl, naphthyl, phenylmethyl or benzyl, phenylethyl, 3,4-methylenedioxyphenyl, m-aminophenyl, m-nitrophenyl, p-aminophenyl, p-nitrophenyl, p-methoxybenzyl, p-fluorobenzyl and p-chlorobenzyl.

As used herein, the designation "∫∫" refers to a bond to a chiral atom for which the stereochemistry is not designated.

The compounds of Formula (I) can be prepared by utilizing procedures and techniques well known and appreciated by one of ordinary skill in the art. A general synthetic scheme for preparing these compounds is set forth in Scheme A wherein all substituents, unless otherwise indicated, are previously defined.

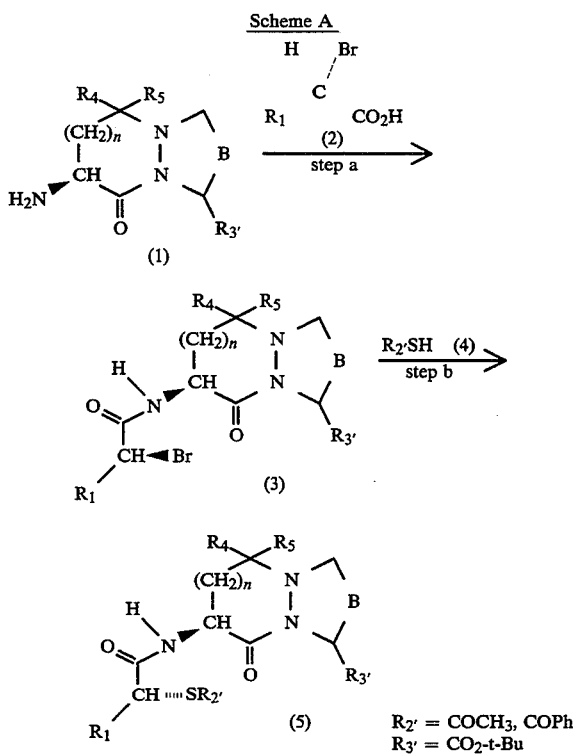

Scheme A $R_{2'}$ = COCH$_3$, COPh
$R_{3'}$ = CO$_2$-t-Bu

In step a, the appropriate amino compound of structure (1) is reacted with the appropriate (S)-bromoacid of structure (2) to give the corresponding (S)-bromoamide compound of structure (3). For example, the appropriate amino compound of structure (1) can be reacted with the appropriate (S)-bromoacid compound of structure (2) in the presence of a coupling reagent such as EEDQ (1-ethoxycarbonyl-2-ethoxy-1,2-dihydroquinoline), DCC (1,3-dicyclohexylcarbodiimide), or diethylcyanophosponate in a suitable aprotic solvent, such as methylene chloride to give the appropriate (S)-bromoamide compound of structure (3).

Alternatively the appropriate amino compound of structure (1) is reacted with the appropriate (R)-bromoacid to give the corresponding (R)-bromoamide compound or the appropriate amino compound of structure (1) is reacted with the appropriate enantiomeric mixture of the bromoacid to give the corresponding enantiomeric mixture of bromoamide as described previously in Scheme A, step a.

In step b, the (S)-bromo functionality of the appropriate (S)-bromoamide compound of structure converted to the corresponding (R)-thioacetate or (R)-thiobenzoate of structure (5a).

For example, the appropriate (S)-bromoamide compound of structure (3) is reacted with thiolacetic acid or thiolbenzoic acid of structure (4) in the presence of a base, such as cesium carbonate. The reactants are typically contacted in a suitable organic solvent such as a mixture of dimethylformamide and tetrahydrofuran. The reactants are typically stirred together at room temperature for a period of time ranging from 1 to 8 hours. The resulting (R)-thioacetate or (R)-thiobenzoate of structure (5a) is recovered from the reaction zone by extractive methods as is known in the art. It may be purified by chromatography.

Alternatively, the (R)-bromo functionality of the appropriate (R)-bromoamide is converted to the corresponding (S)-thioacetate or (S)-thiobenzoate of structure (5b) or the bromo functionality of the appropriate enantiomeric mixture of of the bromoamide is converted to the corresponding enantiomeric mixture of thioacetate or thiobenzoate compounds as described previously in Scheme A, step b.

As summarized in Table 1, the $R_2$ and $R_3$ groups on the thioacetate or thiobenzoate compounds of structures (5a) and (5b) can be manipulated using techniques and procedures well known and appreciated by one of ordinary skill in the art to give the corresponding compounds of structures (6a)–(10a) and (6b)–(10b).

For example, the t-butyl ester functionality of the appropriate (R)-thioacetate or (R)-thiobenzoate compound of structure (5a) can be removed using trifluoroacetic acid to give the appropriate (R)-thioacetate or (R)-thiobenzoate carboxylic acid compound of structure (6a). Similarly, the t-butyl ester functionality of the appropriate (S)-thioacetate or (S)-thiobenzoate compound of structure (5b) can be removed using trifluoroacetic acid to give the (S)-thioacetate or (S)-thiobenzoate carboxylic acid compound of structure (6b).

The (R)-thioacetate or (R)-thiobenzoate functionality of the appropriate (R)-thioacetate or (R)-thiobenzoate carboxylic acid compound of structure (6a) can be removed with lithium hydroxide in a suitable solvent mixture such as tetrahydrofuran and ethanol to give the appropriate (R)-thio carboxylic acid compound of structure (7a). Similarly, the (S)-thioacetate or (S)-thiobenzoate functionality of the appropriate (S)-thioacetate or (S)-thiobenzoate carboxylic acid compound of structure (6b) can be removed with lithium hydroxide in a suitable solvent mixture such as tetrahydrofuran and ethanol to give the appropriate (S)-thio carboxylic acid compound of structure (7b).

Alternatively, the carboxylic acid functionality of the appropriate (R)-thioacetate or (R)-thiobenzoate carboxylic acid compound of structure (6a) can be re-esterified using techniques and procedures well known and appreciated in the art. For example, a (R)-thioacetate or (R)-thiobenzoate compound of structure (5a) can be prepared by treating the (R)-thioacetate or (R)-thiobenzoate carboxylic acid compound of structure (6a) with the appropriate alkyl halide or Ar—Y halide in a suitable aprotic solvent, such as dimethylformamide along with a non-nucleophilic base, such as cesium carbonate. Similarly, the carboxylic acid functionality of the appropriate (S)-thioacetate or (S)-thiobenzoate carboxylic acid compound of structure (6b) can be esterified to the appropriate (S)-thioacetate or (S)-thiobenzoate compound of structure (5b) as described above for the (R)-thioacetate or (R)-thiobenzoate compound of structure (5a).

The (R)-thioacetate or (R)-thiobenzoate functionalities of the appropriate (R)-thioacetate or (R)-thiobenzoate compound of structure (5a) can be hydrolyzed to the corresponding (R)-thiol compounds of structure (Sa) with ammonia in a suitable protic solvent, such as methanol. Similarly, the (S)-thioacetate or (S)-thiobenzoate functionalities of the appropriate (S)-thioacetate or (S)-thiobenzoate compounds of structure (5b) can be hydrolyzed to the corresponding (S)-thiol compounds of structure (8b).

The thiol functionality of the appropriate (R)-thio carboxylic acid compound of structure (7a) can be alkylated using techniques and procedures well known and appreciated in the art. For example, a (R)-pivaloyloxymethylthio carboxylic acid compound of structure (9a) can be prepared by treating the (R)-thio carboxylic acid compound of structure (7a) with the appropriate with chloromethyl pivalate in a suitable aprotic solvent, such as dimethylformamide along with a non-nucleophilic base, such as cesium carbonate. Similarly, the thiol functionality of the appropriate (S)-thio carboxylic acid compound of structure (7b) can be alkylated to the appropriate (S)-pivaloyloxymethylthio carboxylic acid compound of structure (9b) as described above for (9a).

The thiol functionality of the appropriate (R)-thiol compound of structure (Sa) can be alkylated using techniques and procedures well known and appreciated in the art. For example, a (R)-pivaloyloxymethylthio compound of structure (10a) can be prepared by treating the (R)-thiol compound of structure (8a) with the appropriate with chloromethyl pivalate as described above for the conversion of (7a) to (9a). Similarly, the thiol functionality of the appropriate (S)-thiol compound of structure (8b) can be alkylated to the appropriate (S)-pivaloyloxymethylthio compound of structure (10b) as described above for the (R)-pivaloyloxymethylthio compound of structure (10a).

TABLE 1

| MANIPULATION OF $R_2$ AND $R_3$ | | |
|---|---|---|
| Compound | $R_2$ | $R_3$ |
| 5a and 5b | COCH$_3$ or COPh | t-butyloxycarbonyl |
| 6a and 6b | COCH$_3$ or COPh | CO$_2$H |
| 7a and 7b | H | CO$_2$H |
| 8a and 8b | H | alkoxycarbonyl or Ar—Y—O-carbonyl |
| 9a and 9b | —CH$_2$OCOC(CH$_3$)$_3$ | CO$_2$H |
| 10a and 10b | —CH$_2$OCOC(CH$_3$)$_3$ | alkoxycarbonyl or Ar—Y—O-carbonyl |

Starting materials for use in the general synthetic procedures outlined in Scheme A are readily available to one of ordinary skill in the art. For example, certain amino compounds of structure (1) are described in U.S. Pat. No. 4,512,924 of Attwood et al. (Apr. 23, 1985).

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; and "μM" refers to micromolar.

EXAMPLE 1

Preparation of
9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester Scheme A, step a:
9-[(S)-(1-Oxo-2(R)-bromo-3-phenylpropyl)amino]-octahydro-10-oxo-6H-pyridazo[1,2-a][1,2]diazepine-1(S)-carboxylic acid, t-butyl ester Mix D-phenylalanine (186.4 g, 1.128 mol) and 49% hydrobromic acid (372.8 g), cool to −5° C. and add, by dropwise addition, a solution of sodium nitrite (77.9 g) in water (565 mL) over a period of about 1 hour (vigorous gas evolution). Stir at −5° C. to 0° C. for 4 hours, extract into ethyl ether (3×1 L), dry (MgSO$_4$) and evaporate the solvent in vacuo. Purify by chromatography (5% acetic acid/95% methylene chloride) and distillation to give 3-phenyl-2(R)-bromopropionic acid (112 g, 43%); bp 128°–135° C. @0.25 torr.

Mix 3-phenyl-2(R)-bromopropionic acid (3.94 g, 17.2 mmol) and 9(S)-amino-octahydro-10-oxo-6H-pyridazo[1,2-a][1,2]diazepine-1(S)-carboxylic acid, t-butyl ester (3.75 g, 13.2 mmol) in methylene chloride (50 mL). Add EEDQ (4.24 g, 17.7 mmol). Stir at room temperature overnight, dilute with methylene chloride, wash with saturated sodium hydrogen carbonate, water, 1M HCL, water and brine. Dry (MgSO$_4$) and evaporate the solvent in vacuo to give an oily residue. Purify by silica gel chromatography (60:40 hexane/ethyl acetate) to give the title compound as a white foam (4.86 g, 74%).

$^1$H NMR (CDCl$_3$) δ 7.39 (d, 1, J=6.4 Hz), 7.15–7.37 (m, 5), 5.23 (dt, 1, J=6.4, 8.8 Hz), 4.91 (m, 1), 4.39 (dd, 1, J=6.6, 8.0 Hz), 3.54–3.65 (dd, 1, J=6.7, 14.1 Hz), 3.34–3.47 (m, 1), 3.03–3.24 (m, 2), 2.90–3.03 (m, 1), 2.51–2.65 (m, 1), 2.29–2.40 (m, 1), 2.05–2.20 (m, 1), 1.59–1.96 (m, 4), 1.27–1.59 (m, 11); $^{13}$C NMR (CDCl$_3$) δ 172.17, 169,80, 167.02, 137.19, 129.16, 128.32, 126.93, 82.06, 52.54, 51.52, 51.29, 50.85, 50.47, 41.74, 29.64, 27.98, 26.13, 24.95, 16.56.

Scheme A, step b:
9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester Dissolve thiolacetic acid (0.92 mL, 12.9 mmol) in degassed methanol (50 mL) and treat with cesium carbonate (2.00 g, 6.1 mmol). Stir the yellow solution for 30 minutes then evaporate the solvent in vacuo and dry in vacuo for 1.5 hours. Dilute the resulting cesium salt with dimethylformamide (50 mL) and treat with a solution of a mixture of 9-[(S)-(1-oxo-2(R)-bromo-3-phenylpropyl)amino]-octahydro-10-oxo-6H-pyridazo[1,2-a][1,2]diazepine-1(S)-carboxylic acid, t-butyl ester (3.03 g, 6.1 mmol) in dimethylformamide (50 mL). Stir at room temperature for 1.5 hours, dilute with ethyl acetate, wash with water (2×) and brine. Dry (MgSO$_4$), filter and evaporate the solvent in vacuo to give an oily residue. Purify by silca gel chromatography (50:50 hexane/ethyl acetate) to give the title compound as a yellow foam (2.56 g, 85%).

IR (KBr) 3389, 3086, 3065, 3030, 2974, 2933, 2863, 1738, 1690, 1655, 1499, 1447, 1427, 1368, 1154, 1127 cm$^{-1}$; $^1$H NMR (CDCl$_3$) δ 7.12–7.37 (m, 6), 5.14–5.25 (m, 1), 4.87–4.95 (m, 1), 4.29 (t, 1, J=7.5 Hz), 3.25–3.46 (m, 2), 2.88–3.15 (m, 3), 2.49–2.62 (m, 1), 2.25–2.38 (m, 4), 2.08–2.22 (m, 1), 1.32–1.94 (m, 15); $^{13}$C NMR (CDCl$_3$) δ 194.28, 172.21, 169.89, 168.20, 137.55, 129.11, 128.22, 126.61, 81.96, 52.47, 51.51, 50.96, 50.72, 48.35, 36.96, 30.43, 29.63, 27.98, 26.07, 25.02, 16.59; MS (FAB) m/z 490 [M$^+$+H], 434, 414, 392, 358, 267, 211 [base peak]; Anal. Calcd for C$_{25}$H$_{35}$N$_3$O$_5$S: C, 61.33; H, 7.21; N, 8.58; Found: C, 61.20; H, 7.16; N, 8.55.

EXAMPLE 2

Preparation of
9-[(S)-(1-Oxo-2(S)-thio-3-phenylpropyl)amino]-octahydro-10-oxo-6H-pyridazo[1,2-a][1,2]diazepine-1(S)-carboxylic acid, t-butyl ester Dissolve 9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester (0.40 g, 0.82 mmol) in absolute ethanol (20 mL) and saturated ethanolic ammonia (20 mL). Stir the reaction mixture at room temperature for 2 hours, evaporate the solvent in vacuo, dilute with methylene chloride, wash with water and brine. Dry (MgSO$_4$), filter and evaporate the solvent in vacuo to give the title compound as a clear glass (0.30 g, 82%).

IR (KBr) 3389, 3337, 2974, 2934, 2863, 1738, 1645, 1499, 1427, 1368, 1227, 1154 cm$^{-1}$; $^1$H NMR (CDCl$_3$) δ 7.38–7.49 (br d, 1, J=6.6 Hz), 7.14–7.36 (m, 5), 4.86–4.96 (m, 1), 3.50–3.62 (m, 2), 3.35–3.47 (m, 1), 3.23–3.33 (dd, 1, J=6.4, 13.9 Hz), 3.02–3.17 (m, 2), 2.88–3.01 (m, 2), 2.51–2.66 (m, 1), 2.12–2.41 (m, 2), 1.99 (d, 1, J=8.7 Hz), 1.58–1.96 (m, 4), 1.29–1.58 (m, 11); $^{13}$C NMR (CDCl$_3$) δ 172.51, 170.57, 169.90, 137.62, 129.34, 128.31, 126.76, 82.11, 52.63, 51.61, 51,03, 50.86, 44.88, 41.51, 29.72, 28.04, 26.23, 25.01, 16.63; MS (FAB) m/z 448 [M$^+$+H], 414, 392, 358, 211 [base peak]; Anal. Calcd for C$_{23}$H$_{33}$N$_3$O$_4$S: C, 61.72; H, 7.43; N, 9.39; Found: C, 61.58; H, 7.36; N, 9.34.

EXAMPLE 3

Preparation of
9-[(S)-(1-Oxo-2(S)-acetylthio-3phenylpropyl)amino]-octahydro-10-oxo-6H-Pyridazo[1,2-a][1,2]diazepine-1(S)-carboxylic acid The synthesis of 9-[(S)-(1-Oxo-2(S)-acetylthio-3-phenylpropyl)amino]-octahydro-10-oxo-6H-Pyridazo[1,2-a][1,2]diazepine-1(S)-carboxylic acid is the same as that of 9-[(S)-(1-Oxo-2(S)-acetylthio-3-phenylpropyl)amino]-octahydro-10-oxo-6H-pyridazo[1,2-a][1,2]diazepine-1(R)-carboxylic acid described in Example 11, but substituting 9-[(S)-(1-oxo-2(S)-acetylthio-3-phenylpropyl)amino]-octahydro- 10-oxo-6H-pyridazo[1,2-a][1,2]diazepine-1(S)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(R)-carboxylic acid, t-butyl ester.

Yield 58%; IR (film) 3354, 3086, 3063, 3030, 2945, 2870, 1734, 1688, 1651, 1520, 1499, 1454, 1209, 1173, 912, 733 cm$^{-1}$; $^1$H NMR (CDCl$_3$) δ 7.14–7.39 (m, 6), 5.10–5.26 (br s, 1), 4.19–4.46 (br m, 2), 3.17–3.36 (br m, 2), 2.78–3.06 (br m, 4), 2.30 (s, 3), 1.24–2.28 (br m, 11); $^{19}$F NMR (CDCl$_3$) δ −76.30; $^{13}$C NMR (CDCl$_3$) δ 195.03, 174.62, 172.81, 170.11, 137.14, 129.07, 128.33, 126.84, 52.52, 52.07, 51.43, 50.09, 48.39, 36.48, 30.35, 28.92, 25.50, 23.98, 15.36; MS (FAB) m/z 434 [M$^+$+H, base peak], 392, 358, 211; HRMS Calcd for C$_{21}$H$_{28}$N$_3$O$_5$S: 434.1750; Found: 434.1744.

EXAMPLE 4

Preparation of 9-[(S)-(1-Oxo-2(S)-thio-3-phenylpropyl)amino]-octahydro-10-oxo-6H-pyridazo[1,2-a][1,2]diazepine-1(S)-carboxylic acid The synthesis of 9-[(S)-(1-Oxo-2(S)-thio-3-phenylpropyl)amino]-octahydro-10-oxo-6H-pyridazo[1,2-a][1,2]diazepine-1(S)-carboxylic acid is the same as that of 9-[(S)-(1-Oxo-2(S)-acetylthio-3-phenylpropyl)amino]-octahydro-10-oxo-6H-pyridazo[1,2-a][1,2]diazepine-1(R)carboxylic acid described in Example 11, but substituting 9-[(S)-(1-oxo-2(S)-thio-3-phenylpropyl)amino]-octahydro-10-oxo-6H-pyridazo[1,2-a][1,2]diazepine-1(S)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(R)-carboxylic acid, t-butyl ester.

Yield 83%; IR (film) 3318, 3066, 3063, 3030, 2938, 2864, 1728, 1630, 1452, 1211, 1173, 1155, 910, 733 cm$^{-1}$; $^1$H NMR (CDCl$_3$) δ 7.54–7.70 (d, 1, J=7.1 Hz), 6.98–7.45 (m, 5), 5.21– 5.39 (m, 1), 4.92–5.08 (m, 1), 3.56–3.71 (m, 1), 2.86–3.43 (m, 5), 2.48–2.66 (m, 1), 2.31–2.48 (m, 1), 2.08–2.24 (m, 1), 2.04 (d, 1, J=8.7 Hz), 1.66–1.95 (m, 4), 1.33–1.51 (m, 2); $^{19}$F NMR (CDCl$_3$) δ −76.30; $^{13}$C NMR (CDCl$_3$) δ 173.74, 172.95, 171.27, 136.90, 128.95, 128.00, 126.54, 51.97, 51.06, 50.72, 49.40, 44.23, 40.95, 28.97, 25.39, 24.08, 15.83; MS (FAB) m/z 392 [M$^+$+H, base peak], 358, 211; HRMS Calcd for C$_{19}$H$_{26}$N$_3$O$_4$S: 392.1644; Found: 392.1635.

EXAMPLE 5

Preparation of 9-[(S)-(1-Oxo-2(S)-acetylthio-3-phenylpropyl)amino]-octahydro-10-oxo-6H-pyridazo[1,2-a][1,2]diazepine-1(S)-carboxylic acid, benzyl ester Dissolve 9-[(S)-(1-oxo-2(S)-acetylthio-3-phenylpropyl)amino]-octahydro-10-oxo-6H-pyridazo[1,2-a][1,2]diazepine-1(S)-carboxylic acid (4.33 mmol) in methylene chloride (25 mL) and dry over anhydrous MgSO$_4$. Filter and wash with methylene chloride (3×200 mL). Evaporate in vacuo to a residue. Dissolve the residue in anhydrous dimethylformamide (25 mL) and place under nitrogen atmosphere. Add cesium carbonate (1.65 g, 5.0 mmole) in one portion. Stir for 45 minutes at ambient temperature. Add benzyl bromide (550mg, 5.0 mmol). Stir the resulting mixture at ambient temperature for 18 hours. Quench the reaction with ethyl acetate (50 mL) and water (50 mL). Separate the organic phase and wash with water (7×50 mL), ¼ saturated potassium hydrogen carbonate (50 mL), water (50 mL), and saturated sodium chloride (50 mL). Dry (MgSO$_4$), filter and evaporate in vacuo to yield the title compounds.

EXAMPLE 6

Preparation of 9-[(S)-(1-Oxo-2(S)-thio-3-phenylpropyl)amino]-octahydro-10-oxo-6H-pyridazo[1,2-a][1,2]diazepine-1(S)-carboxylic acid, benzyl ester Stir 9-[(S)-(1-oxo-2(S)-acetylthio-3-phenylpropyl)amino]-octahydro-10-oxo-6H-pyridazo[1,2-a][1,2]diazepine-1(S)-carboxylic acid, benzyl ester (4 mmol) and saturated methanolic ammonia at ambient temperature until hydrolysis is complete. Evaporate the solvent in vacuo and purify by silica gel chromatography to give the title compounds.

EXAMPLE 7

9-[(S)-(1-Oxo-2(S)-pivaloyloxymethylthio-3-phenylpropyl)amino]-octahydro-10-oxo-6H-pyridazo[1,2-a][1,2]diazepine-1(S)-carboxylic acid Dissolve 9-[(S)-(1-oxo-2(S)-thio-3-phenylpropyl)amino]-octahydro-10-oxo-6H-pyridazo[1,2-a][1,2]diazepine-1(S)-carboxylic acid (0.28 mmol) in methylene chloride (1 mL) and dry over anhydrous MgSO$_4$ (60mg). Filter and wash with methylene chloride (3×20 mL). Evaporate in vacuo to a residue. Dissolve the residue in anhydrous dimethylformamide (10 mL) and place under nitrogen atmosphere. Add cesium carbonate (100mg, 0.3 mmol) in one portion. Stir for 45 minutes at ambient temperature. Add chloromethyl pivalate (42 g, 0.28 mmol). Stir the resulting mixture at ambient temperature for 18 hours. Quench the reaction with ethyl acetate (3 mL) and water (10 mL). Separate the organic phase and wash with water (7×10 mL), ¼ saturated potassium hydrogen carbonate (10 mL), water (10 mL), and saturated sodium chloride (10 mL). Dry (MgSO$_4$), filter and evaporate in vacuo to yield the title compounds.

EXAMPLE 8

9-[(S)-(1-Oxo-2(S)-pivaloyloxymethylthio-3-phenylpropyl)amino]-octahydro-10-oxo-6H-pyridazo[1,2-a][1,2]diazepine-1(S)-carboxylic acid, benzyl ester Dissolve 9-[(S)-(1-oxo-2(S)-thio-3-phenylpropyl)amino]-octahydro-10-oxo-6H-pyridazo[1,2-a][1,2]diazepine-1(S)-carboxylic acid, benzyl ester (0.28 mmol) in methylene chloride (1 mL) and dry over anhydrous MgSO$_4$ (60mg). Filter and wash with methylene chloride (3×20 mL). Evaporate in vacuo to a residue. Dissolve the residue in anhydrous dimethylformamide (10 mL) and place under nitrogen atmosphere. Add cesium carbonate (100mg, 0.3 mmol) in one portion. Stir for 45 minutes at ambient temperature. Add chloromethyl pivalate (42 g, 0.28 mmol). Stir the resulting mixture at ambient temperature for 18 hours. Quench the reaction with ethyl acetate (3 mL) and water (10 mL). Separate the organic phase and wash with water (7×10 mL), ¼ saturated potassium hydrogen carbonate (10 mL), water (10 mL), and saturated sodium chloride (10 mL). Dry (MgSO$_4$), filter and evaporate in vacuo to yield the title compounds.

EXAMPLE 9

Preparation of 9-[(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester Scheme A, step a:
9-[(S)-(1-Oxo-2(R)-bromo-3-phenylpropyl)amino]-octahydro-10-oxo-6H-pyridazo[1,2-a][1,2]diazepine-1(R)-carboxylic acid, t-butyl ester The synthesis of 9-[(S)-(1-Oxo-2(R)-bromo-3-phenylpropyl)amino]-octahydro-10-oxo-6H-pyridazo[1,2-a][1,2]diazepine-1(R)-carboxylic acid, t-butyl ester is the same as for 9-[(S)-(1-Oxo-2(R)-bromo-3-phenylpropyl)amino]-octahydro-10-oxo-6H-pyridazo[1,2-a][1,2]diazepine-1(S)-carboxylic acid, t-butyl ester described in Example 1, Step a, but substituting 9(S)-amino-octahydro-10-oxo-6H-pyridazo[1,2-a][1,2]diazepine-1(R)-carboxylic acid, t-butyl ester for 9(S)-amino-octahydro-10-oxo-6H-pyridazo[1,2-a][1,2]diazepine-1(S)-carboxylic acid, t-butyl ester.

Yield 84%; IR (KBr) 3351, 3059, 3030, 3000, 2974, 2951, 2928, 1707, 1690, 1676, 1541, 1452, 1368, 1304, 1165, 702 cm$^{-1}$; $^1$H NMR (CDCl$_3$) δ 7.08–7.51 (m, 6), 5.06–5.23 (br m, 1), 4.31–4.50 (br m, 1), 4.07–4.30 (br s, 1), 3.45–3.60 (m, 1), 3.14–3.38 (br m, 2), 2.76–3.07 (br m, 3), 1.15–2.28 (m, 17); $^{13}$C NMR (CDCl$_3$) δ 171.69, 169.65, 166.78, 136.99, 129.28, 128.31, 126.98, 81.66, 52.82, 51.69, 51.02, 50.44, 41.87, 41.23, 29.35, 27.96, 25.96, 24.40, 15.80; Anal. Calcd for C$_{23}$H$_{32}$BrN$_3$O$_4$: C, 55.87; H, 6.52; N, 8.50; Found: C, 56.07; H, 6.49; N, 8.48.

Scheme A, step b:
9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester The synthesis of 9-[(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester is the same as for 9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester described in Example 1, Step b, but substituting 9-[(S)-(1-oxo-2(R)-bromo-3-phenylpropyl)amino]-octahydro-10-oxo-6H-pyridazo[1,2-a][1,2]diazepine-1(R)-carboxylic acid, t-butyl ester for 9-[(S)-(1-oxo-2(R)-bromo-3-phenylpropyl)amino]-octahydro-10-oxo-6H-pyridazo[1,2-a][1,2]diazepine-1(S)-carboxylic acid, t-butyl ester.

Yield 75%; IR (CHCl$_3$) 3391, 3065, 3032, 3009, 2982, 2945, 2872, 1734, 1684, 1655, 1507, 1454, 1370, 1306, 1236, 1154, 955 cm$^{-1}$; $^1$H NMR (CDCl$_3$) δ 7.16–7.39 (m, 6), 5.07–5.23 (br m, 1), 4.12–4.32 (br m, 2), 3.19–3.38 (br m, 2), 2.76–3.04 (br m, 4), 2.28 (s, 3), 1.19–2.23 (br m, 17; MS (CI, 70 ev) m/z 490 [M$^+$+H]434 [base peak]; Anal. Calcd for C$_{25}$H$_{35}$N$_3$O$_5$S: C, 61.33; H, 7.21; N, 8.58; Found: C, 61.23; H, 7.12; N, 8.57.

EXAMPLE 10

Preparation of
9-[(S)-(1-Oxo-2(S)-thio-3-phenylpropyl)amino]-octahydro-10-oxo-6H-pyridazo[1,2-a][1,2]diazepine-1(R)-carboxylic acid, t-butyl ester The synthesis of 9-[(S)-(1-Oxo-2(S)-thio-3-phenylpropyl)amino]-octahydro-10-oxo-6H-pyridazo[1,2-a][1,2]diazepine-1(R)-carboxylic acid, t-butyl ester is the same as that of 9-[(S)-(1-Oxo-2(S)-thio-3-phenylpropyl)amino]-octahydro-10-oxo-6H-pyridazo[1,2a][1,2]diazepine-1(S)-carboxylic acid, t-butyl ester described in Example 2, but substituting 9-[(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(S)-carboxylic acid, t-butyl ester.

Yield 81%; IR (KBr) 3393, 2974, 2936, 2870, 1738, 1653, 1499, 1452, 1368, 1154 cm$^{-1}$; $^1$H NMR (CDCl$_3$) δ 7.03–7.43 (m, 6), 5.09–5.34 (br m, 1), 4.08–4.29 (br s, 1), 3.46–3.58 (m, 1), 3.20–3.39 (br m, 2), 2.75–3.14 (br m, 5), 1.18–2.30 (br m, 17); $^{13}$C NMR (CDCl$_3$) δ 172.15, 170.39, 169.70, 137.16, 129.34, 128.31, 126.78, 81.60, 53.05, 52.92, 51.34, 50.38, 44.76, 41.44, 29.61, 27.98, 26.15, 24.37, 15.79; MS (FAB) m/z 448 [M$^+$+H, base peak], 414, 392, 358, 211; Anal. Calcd for C$_{25}$H$_{33}$N$_3$O$_4$S: C, 61.72; H, 7.43; N, 9.39; Found: C, 61.40; H, 7.35; N, 9.34.

EXAMPLE 11

Preparation of
9-[(S)-(1-Oxo-2(S)-acetylthio-3-phenylpropyl)amino]-octahydro-10-oxo-6H-pyridazo[1,2-a][1,2]diazepine-1(R)-carboxylic acid Dissolve 9-[(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester (1.33 g, 2.7 mmol) and anisole (1 mL, excess) in methylene chloride (20 mL) and treat with trifluoroacetic acid (5 mL). Stir for 6 hours at room temperature, evaporate the solvent in vacuo triturate the residue with hexane (3×) and dry in vacuo overnight. Dissolve the resulting gum in a minimal amount of methylene chloride and precipitate from hexane. Decant the solvent, dry in vacuo and triturate from hexane to give the title compound as a light tan powder (0.88 g, 59%).

IR (film) 3335, 3088, 3065, 3030, 2940, 2864, 1780, 1734, 1694, 1634, 1522, 1454, 1356, 1211, 1171, 1130, 913, 733 cm$^{-1}$; $^1$H NMR (CDCl$_3$) δ 7.40–7.50 (d, 1, J=7.1 Hz), 7.13–7.35 (m, 5), 5.20–5.34 (m, 1), 4.95–5.04 (m, 1), 4.31 (t, 1, J=7.3 Hz), 3.22–3.41 (m, 2), 2.90–3.22 (m, 3), 2.48–2.64 (m, 1), 2.35–2.47 (m, 1), 2.32 (s, 3), 2.04–2.21 (m, 1), 1.67–1.98 (m, 4), 1.30–1.52 (m, 3); $^{19}$F NMR (CDCl$_3$) δ −76.28; $^{13}$C NMR (CDCl$_3$) δ 198.65, 174.28, 173.13, 170.17, 137.13, 129.11, 128.36, 126.86, 52.20, 51.43, 51.13, 49.74, 48.43, 36.62, 30.41, 29.22, 25.61, 24.37, 16.13; MS (FAB) m/z 434 [M$^+$+H, base peak], 358, 211; HRMS Calcd for C$_{21}$H$_{28}$N$_3$O$_5$S: 434.1750; Found: 434.1733.

EXAMPLE 12

Preparation of
9-[(S)-(1-Oxo-2(S)-thio-3-phenylpropyl)amino]-octahydro-10-oxo-6H-pyridazo[1,2-a][1,2]diazepine-1(R)-carboxylic acid The synthesis of 9-[(S)-(1-Oxo-2(S)-thio-3-phenylpropyl)amino]-octahydro-10-oxo-6H-pyridazo[1,2-a][1,2]diazepine-1(R)-carboxylic acid is the same as that of 9-[(S)-(1-Oxo-2(S)-acetylthio-3-phenylpropyl)amino]-octahydro-10-oxo-6H-pyridazo[1,2-a][1,2]diazepine-1(R)-carboxylic acid described in Example 11, but sustituting 9-[(S)-(1-oxo-2(S)-thio-3-phenylpropyl)amino]-octahydro-10-oxo-6H-pyridazo[1,2-a][1,2]diazepine-1(S)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(R)-carboxylic acid, t-butyl ester.

Yield 74%; IR (film) 3339, 3086, 3063, 3030, 2945, 2870, 1778, 1728, 1635, 1454, 1209, 1173, 910, 733 cm$^{-1}$; $^1$H NMR (CDCl$_3$) δ 7.04–7.81 (br m, 6), 5.12–5.36 (br m, 1), 4.20–4.47 (br s, 1), 3.64 (q, 1, J=7.4 Hz), 2.74–3.43 (br m, 6), 1.23–2.35 (br m, 9); $^{19}$F NMR (CDCl$_3$) δ−76.31; $^{13}$C NMR (CDCl$_3$) δ 174.24, 172.93, 171.66, 137.13, 129.32, 128.32, 126.91, 52.62, 52.16, 51.38, 55.20. 44.55, 41.17, 29.11, 25.85, 23.93, 15.35; MS (FAB) m/z 392 [M$^+$+H, base peak], 358, 211; HRMS Calcd for C$_{19}$H$_{26}$N$_3$O$_4$S: 392.1644; Found: 392.1663.

EXAMPLE 13

Preparation of
9-((S)-(1-Oxo-2(S)-acetylthio-3-phenylpropyl)amino)-octahydro-6,10-dioxo-6H-pyridazo[1,2-a][1,2]diazepine-1(S)-carboxylic acid, t-butyl ester Scheme A, step a:
9-[(S)-(1-Oxo-2(R)-bromo-3-phenylpropyl)amino]-octahydro-6,10-dioxo-6H-pyridazo[1,2-a][1,2]diazepine-1(S)-carboxylic acid, t-butyl ester The synthesis of 9-[(S)-(1-Oxo-2(R)-bromo-3-phenylpropyl)amino]-octahydro-6,10-dioxo-6H-pyridazo[1,2-a][1,2]diazepine-1(R)-carboxylic acid, t-butyl ester is the same as for 9-[(S)-(1-Oxo-2(R)- bromo-3-phenylpropyl)amino]-octahydro-10-oxo-6H-pyridazo[1,2-a][1,2]diazepine-1(S)-carboxylic acid, t-butyl ester described in Example 1, Step a, but substituting 9(S)-amino-octahydro-6,10-dioxo-6H-pyridazo[1,2-a][1,2]diazepine-1(S)-carboxylic acid, t-butyl ester for 9(S)-amino-octahydro-10-oxo-6H-pyridazo[1,2-a][1,2]diazepine-1(S)-carboxylic acid, t-butyl ester.

Yield 84%; IR (KBr) 3385, 3337, 2978, 2936, 1736, 1676, 1518, 1456, 1445, 1425, 1370, 1339, 1310, 1273, 1250, 1235, 1157, 1132 748 cm$^{-1}$; $^1$H NMR (CDCl$_3$) δ 7.16–7.42 (m, 5), 6.93 (d, 1, J=7.2 Hz), 5.23 (dd, 1, J=3.0, 6.0 Hz), 4.75–4.89 (m, 1), 4.56–4.68 (dt, 1, J=3.6, 12.9 Hz), 4.39 (t, 1, J=7.5 Hz), 3.36–3.63 (m, 2), 3.13–3.25 (dd, 1, J=7.9, 14.2 Hz), 2.79–2.94 (m, 1), 2.58–2.76 (m, 1), 2.16–2.40 (m, 2), 1.77–1.96 (m, 1), 1.36–1.77 (m, 12); $^{13}$C NMR (CDCl$_3$) δ 171.47, 169.43 168.00, 167.39, 136.91, 129.19, 128.43, 127.13, 83.16, 53.35, 49.88, 48.98, 41.74, 41.32, 31.05, 30.02, 28.06, 25.69, 20.20; MS (FAB) m/z 508 [M$^+$+H]452 [base peak], 428, 408, 372, 197; Anal. Calcd for C$_{23}$H$_{30}$BrN$_3$O$_5$: C, 54.34; H, 5.95; N, 8.26; Found: C, 54.25; H, 6.02; N, 8.41.

Scheme A, step b:
9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester The synthesis of 9-[(S)-(1-Oxo-2(S)-acetylthio-3-phenylpropyl)amino]-octahydro-6,10-dioxo-6H-pyridazo[1,2-a][1,2]diazepine-1(S)-carboxylic acid, t-butyl ester is the same as for 9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester described in Example 1, step b, but substituting 9-[(S)-(1-oxo-2(R)-bromo-3-phenylpropyl)amino]-octahydro-6,10-dioxo-6H-pyridazo[1,2-a][1,2]diazepine-1(S)-carboxylic acid, t-butyl ester for 9-[(S)-(1-oxo-2(R)-bromo-3-phenylpropyl)amino]-octahydro-10-oxo-6H-pyridazo[1,2-a][1,2]diazepine-1(S)-carboxylic acid, t-butyl ester.

Yield 84%; IR (film) 3325, 3086, 3063, 3007, 2980, 2938, 1736, 1678, 1518, 1456, 1445, 1424, 1370, 1341, 1312, 1273, 1250, 1233, 1155, 1130, 754 cm$^{-1}$; $^1$H NMR (CDCl$_3$) δ 7.14–7.40 (m, 5), 6.90–7.02 (d, 1, J=7.2 Hz), 5.20–5.30 (m, 1), 4.70–4.86 (m, 1), 4.27 (t, 1, J=7.5 Hz), 3.37–3.54 (m, 1), 3.23–3.36 (dd, 1, J=7.5, 14.1 Hz), 2.94–3.07 (dd, 1, J=7.8, 14.1 Hz), 2.64–2.88 (m, 2), 2.15–2.41 (m, 5), 1.56–1.92 (m, 4), 1.45 (s, 9); $^{13}$C NMR (CDCl$_3$) δ 195.13, 171.58, 169.43, 168.06, 137.27, 129.11, 128.31, 126.76, 83.04, 53,10, 48.72, 47.75, 41.25, 36.19, 30.83, 30.45, 30.02, 28.03, 25.73, 20.20; MS (CI, 70 ev) m/z 504 [M$^+$+H]448 [base peak], 374; HRMS Calcd for C$_{25}$H$_{34}$N$_3$O$_6$S: 504.2168, Found: 504.2193; Anal. Calcd for C$_{25}$H$_{33}$N$_3$O$_6$S: C, 59.62; H, 6.60; N, 8.34; Found: C, 59.39; H, 6.58; N, 8.17.

EXAMPLE 14

Preparation of 9-((S)-(1-Oxo-2(S)-thio-3-phenylpropyl)amino)-octahydro-6,10-dioxo-6H-pyridazo[1,2-a][1,2]diazepine-1(S)-carboxylic acid, t-butyl ester The synthesis of 9-((S)-(1-Oxo-2(S)-thio-3-phenylpropyl)amino)-octahydro-6,10-dioxo-6H-pyridazo[1,2-a][1,2]diazepine-1(S)-carboxylic acid, t-butyl ester is the same as that of 9-[(S)-(1-Oxo-2(S)-thio-3-phenylpropyl)amino]-octahydro-10-oxo-6H-pyridazo[1,2-a][1,2]diazepine-1(S)-carboxylic acid, t-butyl ester described in Example 2, but substituting 9-[(S)-(1-Oxo-2(S)-acetylthio-3-phenylpropyl)amino]-octahydro-6,10-dioxo-6H-pyridazo[1,2-a][1,2]diazepine-1(R)-carboxylic acid, t-butyl ester for 9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester.

Yield 88%; IR (KBr) 3349, 2978, 2936, 1736, 1676, 1518, 1499, 1456, 1445, 1424, 1370, 1273, 1250, 1231, 1157, 1132 cm$^{-1}$; $^1$H NMR (CDCl$_3$) δ 7.02–7.43 (m, 6), 5.18–5.29 (m, 1), 4.74–4.89 (m, 1), 4.55–4.68 (m, 1), 3.55–3.68 (m, 1), 3.36–3.55 (m, 1), 3.10–3.30 (m, 2), 2.66–2.92 (m, 2), 2.17–2.40 (m, 2), 1.99 (d, 1, J=8.9 Hz), 1.21–1.93 (m, 13); $^{13}$C NMR (CDCl$_3$) δ 171.58, 170.83, 169.69, 168.02, 137.08, 129.38, 128.34, 126.93, 83.15, 53.28, 48.79. 44.66, 41.35, 41.21, 31.00, 30.06, 28.07, 25.73, 20.26; MS (FAB) m/z 462 [M$^+$+H], 429, 406 [base peak], 372; Anal. Calcd for C$_{23}$H$_{31}$N$_3$O$_5$S: C, 59.84; H, 6.77; N, 9.10; Found: C, 59.59; H, 6.73; N, 9.10.

EXAMPLE 15

Preparation of
9-((S)-(1-Oxo-2(S)-acetylthio-3-phenylpropyl)amino)-octahydro-6,10-dioxo-6H-pyridazo[1,2-a][1,2]diazepine-1(S)-carboxylic acid The synthesis of 9-((S)-(1-Oxo-2(S)-acetylthio-3-phenylpropyl)amino)-octahydro-6,10-dioxo-6H-pyridazo[1,2-a][1,2]diazepine-1(S)-carboxylic acid is the same as that of 9-[(S)-(1-Oxo-2(S)-acetylthio-3-phenylpropyl)amino]-octahydro-10-oxo-6H-pyridazo[1,2-a][1,2]diazepine-1(R)-carboxylic acid described in Example 11, but sustituting 9-[(S)-(1-oxo-2(S)-acetylthio-3-phenylpropyl)amino]-octahydro-6,10-dioxo-6H-pyridazo[1,2-a][1,2]diazepine-1(S)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(R)-carboxylic acid, t-butyl ester.

Yield 58%; IR (CHCl$_3$) 3380, 3088, 3065, 3032, 3011, 2957, 2938, 1782, 1723, 1680, 1520, 1458, 1447, 1425, 1233, 1171, 1134 cm$^{-1}$; $^1$H NMR (CDCl$_3$) δ 7.08–7.39 (m, 6), 5.36–5.47 (m, 1), 4.74–4.88 (m, 1), 4.53–4.68 (m, 1), 4.29 (t, 1, J=7.4 Hz), 3.18–3.48 (m, 2), 2.83–3.07 (m, 2), 2.58–2.79 (m, 1), 2.18–2.49 (m, 5), 1.61–2.02 (m, 4); $^{13}$C NMR (CDCl$_3$) δ 195.44, 172.87, 172.55, 170.63, 169.37, 136.83, 129.07, 128.42, 126.97, 52.62, 48.83, 47.96, 41.78, 36.12, 30.63, 30.46, 29.54, 25.15, 20.29; MS (FAB) m/z 448 [M$^+$+H, base peak], 406; HRMS Calcd for C$_{21}$H$_{26}$N$_3$O$_6$S: 448.1542; Found: 448.1523.

EXAMPLE 16

Preparation of 9-((S)-(1-Oxo-2(S)-thio-3-phenylpropyl)amino)-octahydro-6,10-dioxo-6H-pyridazo[1,2-a][1,2]diazepine-1(S)-carboxylic acid The synthesis of 9-((S)-(1-Oxo-2(S)-thio-3-phenylpropyl)amino)-octahydro-6,10-dioxo-6H-pyridazo[1,2-a][1,2]diazepine-1(S)-carboxylic acid is the same as that of 9-[(S)-(1-Oxo-2(S)-acetylthio-3-phenylpropyl)amino]-octahydro-10-oxo-6H-pyridazo[1,2-a][1,2]diazepine-1(R)-carboxylic acid described in Example 11, but sustituting 9-[(S)-(1-oxo-2(S)-thio-3-phenylpropyl)amino]-octahydro-6,10-dioxo-6H-pyridazo[1,2-a][1,2]diazepine-1(S)-carboxylic acid, t-butyl ester for 9-[(S)-(1-oxo-2(S)-acetylthio-3-phenylpropyl)amino]-octahydro-10-oxo-6H-pyridazo[1,2-a][1,2]diazepine-1(R)-carboxylic acid, t-butyl ester.

Yield 95%; IR (CHCl$_3$) 3347, 3088, 3065, 3034, 3009, 2957, 2940, 2872, 1782, 1726, 1672, 1516, 1456, 1447, 1429, 1277, 1235, 1173 cm$^{-1}$; $^1$H NMR (CDCl$_3$) δ 7.06–7.49 (m, 6), 5.35–5.47 (dd, 1, J=2.7, 3.1 Hz), 4.77–4.93 (m, 1), 4.53–4.71 (m, 1), 3.63–3.76 (m, 1), 3.31–3.48 (m, 1), 3.09–3.31 (m, 2), 2.82–2.98 (m, 1), 2.61–2.89 (m, 1), 2.24–2.45 (m, 2), 2.05 (d, 1, J=8.7 Hz), 1.61–2.01 (m, 4); $^{13}$C NMR (CDCl$_3$) δ 172.73, 172.25, 169.59, 136.67, 129.31, 128.42, 127.08, 52.69, 48.87, 44.42, 41.79, 41.07, 30.73, 29.60, 25.16, 20.25; MS (FAB) m/z 406 [M+ +H, base peak]; HRMS Calcd for C$_{19}$H$_{24}$N$_3$O$_5$S: 406.1437; Found: 406.1427.

The following compounds can be prepared by procedures analogous to those described above in Examples 1–16:

8-((S)-(1-Oxo-2(R)-acetylthio-3-phenylpropyl)amino)-2,3,6,7,8,9-hexahydro-5,9-dioxo-1H,5H-pyrazolo[1,2-a][1,2]diazepine-1-carboxylic acid, t-butyl ester;

8-((S)-(1-Oxo-2(R)-acetylthio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-thio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-thio-3-phenylpropyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(R)-pivaloyloxymethylthio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-pivaloyloxymethylthio-3-phenylpropyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(R)-acetylthio-3-(3,4-methylenedioxyphenyl)propyl)amino)-2,3,6,7 8,9-hexahydro-5,9-dioxo-1H,5H-pyrazolo[1,2-a][1,2]diazepine-1-carboxylic acid, t-butyl ester;

8-((S)-(1-Oxo-2(R)-acetylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-thio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-thio-3-(3,4-methylenedioxyphenyl)propyl)amino)-2,3,6,7 8,9-hexahydro-5,9-dioxo-1H,5H-pyrazolo[1,2-a][1,2]diazepine-1-carboxylic acid, benzyl ester;

8-((S)-(1-Oxo-2(R)-pivaloyloxymethylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid;

8-((S)-(1-Oxo-2(R)-pivaloyloxymethylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(R)-acetylthio-3-phenylpropyl)amino)-octahydro-6,9-dioxopyridazo[1,2-a]pyridazine-1-carboxylic acid, t-butyl ester;

8-((S)-(1-Oxo-2(R)-acetylthio-3-phenylpropyl)amino)-octahydro-6,9-dioxopyridazo[1,2-a]pyridazine-1-carboxylic acid;

8-((S)-(1-Oxo-2(R)-thio-3-phenylpropyl)amino)-octahydro-6,9-dioxopyridazo[1,2-a]pyridazine-1-carboxylic acid;

8-((S)-(1-Oxo-2(R)-thio-3-phenylpropyl)amino)-octahydro-6,9-dioxopyridazo[1,2-a]pyridazine-1-carboxylic acid, benzyl ester;

8-((S)-(1-Oxo-2(R)-pivaloyloxymethylthio-3-phenylpropyl)amino)-octahydro-6,9-dioxopyridazo[1,2-a]pyridazine-1-carboxylic acid;

8-((S)-(1-Oxo-2(R)-pivaloyloxymethylthio-3-phenylpropyl)amino)-octahydro-6,9-dioxopyridazo[1,2-a]pyridazine-1-carboxylic acid, benzyl ester;

8-((S)-(1-Oxo-2(R)-acetylthio-3-(3,4-methylenedioxyphenyl)propyl)amino)-octahydro-6,9dioxopyridazo[1,2-a]pyridazine-1-carboxylic acid, t-butyl ester;

8-((S)-(1-Oxo-2(R)-acetylthio-3-(3,4-methylenedioxyphenyl)propyl)amino)-octahydro-6,9dioxopyridazo[1,2-a]pyridazine-1-carboxylic acid;

8-((S)-(1-Oxo-2(R)-thio-3-(3,4-methylenedioxyphenyl)propyl)amino)-octahydro-6,9dioxopyridazo[1,2-a]pyridazine-1-carboxylic acid;

8-((S)-(1-Oxo-2(R)-thio-3-(3,4-methylenedioxyphenyl)propyl)amino)-octahydro-6,9dioxopyridazo[1,2-a]pyridazine-1-carboxylic acid, benzyl ester;

8-((S)-(1-Oxo-2(R)-pivaloyloxymethylthio-3-(3,4-methylenedioxyphenyl)propyl)amino)-octahydro-6,9dioxopyridazo[1,2-a]pyridazine-1-carboxylic acid;

8-((S)-(1-Oxo-2(R)-pivaloyloxymethylthio-3-(3,4-methylenedioxyphenyl)propyl)amino)-octahydro-6,9dioxopyridazo[1,2-a]pyridazine-1-carboxylic acid, benzyl ester;

8-((S)-(1-Oxo-2(R)-acetylthio-3-phenylpropyl)amino)-octahydro-9-oxopyridazo[1,2-a]pyridazine-1-carboxylic acid, t-butyl ester;

8-((S)-(1-Oxo-2(R)-acetylthio-3-phenylpropyl)amino)-octahydro-9-oxopyridazo[1,2-a]pyridazine-1-carboxylic acid;

8-((S)-(1-Oxo-2(R)-thio-3-phenylpropyl)amino)-octahydro-9-oxopyridazo[1,2-a]pyridazine-1-carboxylic acid;

8-((S)-(1-Oxo-2(R)-thio-3-phenylpropyl)amino)-octahydro-9-oxopyridazo[1,2-a]pyridazine-1-carboxylic acid, benzyl ester;

8-((S)-(1-Oxo-2(R)-pivaloyloxymethylthio-3-phenylpropyl)amino)-octahydro-9-oxopyridazo[1,2-a]pyridazine-1-carboxylic acid;

8-((S)-(1-Oxo-2(R)-pivaloyloxymethylthio-3-phenylpropyl)amino)-octahydro-9-oxopyridazo[1,2-a]pyridazine-1-carboxylic acid, benzyl ester;

8-((S)-(1-Oxo-2(R)-acetylthio-3-(3,4-methylenedioxyphenyl)propyl)amino)-octahydro-9oxopyridazo[1,2-a]pyridazine-1-carboxylic acid, t-butyl ester;

8-((S)-(1-Oxo-2(R)-acetylthio-3-(3,4-methylenedioxyphenyl)propyl)amino)-octahydro-9oxopyridazo[1,2-a]pyridazine-1-carboxylic acid;

8-((S)-(1-Oxo-2(R)-thio-3-(3,4-methylenedioxyphenyl)propyl)amino)-octahydro-9oxopyridazo[1,2-a]pyridazine-1-carboxylic acid;

8-((S)-(1-Oxo-2(R)-thio-3-(3,4-methylenedioxyphenyl)propyl)amino)-octahydro-9oxopyridazo[1,2-a]pyridazine-1-carboxylic acid, benzyl ester;

8-((S)-(1-Oxo-2(R)-pivaloyloxymethylthio-3-(3,4-methylenedioxyphenyl)propyl)amino)-octahydro-9oxopyridazo[1,2-a]pyridazine-1-carboxylic acid;

8-((S)-(1-Oxo-2(R)-pivaloyloxymethylthio-3-(3,4-methylenedioxyphenyl)propyl)amino)-octahydro-9oxopyridazo[1,2-a]pyridazine-1-carboxylic acid, benzyl ester;

8-((S)-(1-Oxo-2(R)-acetylthio-3-phenylpropyl)amino)-1,4,5,7,8,9-hexahydro-6,9-dioxopyridazo[1,2-a]pyridazine-1-carboxylic acid, t-butyl ester;

8-((S)-(1-Oxo-2(R)-acetylthio-3-phenylpropyl)amino)-1,4,5,7,8,9-hexahydro-6,9-dioxopyridazo[1,2-a]pyridazine-1-carboxylic acid;

8-((S)-(1-Oxo-2(R)-thio-3-phenylpropyl)amino)-1,4,5,7,8,9-hexahydro-6,9-dioxopyridazo[1,2-a]pyridazine-1-carboxylic acid;

8-((S)-(1-Oxo-2(R)-thio-3-phenylpropyl)amino)-1,4,5,7,8,9-hexahydro-6,9-dioxopyridazo[1,2-a]pyridazine-1-carboxylic acid, benzyl ester;

8-((S)-(1-Oxo-2(R)-pivaloyloxymethylthio-3-phenylpropyl)amino)-1,4,5,7,8,9-hexahydro-6,9-dioxopyridazo[1,2-a]pyridazine-1-carboxylic acid;

8-((S)-(1-Oxo-2(R)-pivaloyloxymethylthio-3-phenylpropyl)amino)-1,4,5,7,8,9-hexahydro-6,9-dioxopyridazo[1,2-a]pyridazine-1-carboxylic acid, benzyl ester;

8-((S)-(1-Oxo-2(R)-acetylthio-3-(3,4-methylenedioxyphenyl)propyl)amino)-1,4,5,7,8,9-hexahydro-6,9-dioxopyridazo[1,2-a]pyridazine-1-carboxylic acid, t-butyl ester;

8-((S)-(1-Oxo-2(R)-acetylthio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(R)-thio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(R)-thio-3-(3,4-methylenedioxyphenyl)propyl)amino)-1,4,5,7,8,9-hexahydro-6,9-dioxopyridazo[1,2-a]pyridazine-1-carboxylic acid, benzyl ester;

8-((S)-(1-Oxo-2(R)-pivaloyloxymethylthio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(R)-pivaloyloxymethylthio-3-(3,4-methylenedioxyphenyl)propyl)amino)-1,4,5,7,8,9-hexahydro-6,9-dioxopyridazo[1,2-a]pyridazine-1-carboxylic acid, benzyl ester;

2-((S)-(1-Oxo-2(R)-acetylthio-3-phenylpropyl)amino)-hexahydro-3-oxo-1H-pyrazolo[1,2-a]pyridazine-5-carboxylic acid, t-butyl ester;

2-((S)-(1-Oxo-2(R)-acetylthio-3-phenylpropyl)amino)-hexahydro-3-oxo-1H-pyrazolo[1,2-a]pyridazine-5-carboxylic acid;

2-((S)-(1-Oxo-2(R)-thio-3-phenylpropyl)amino)-hexahydro-3-oxo-1H-pyrazolo[1,2-a]pyridazine-5-carboxylic acid;

2-((S)-(1-Oxo-2(R)-thio-3-phenylpropyl)amino)-hexahydro-3-oxo-1H-pyrazolo[1,2-a]pyridazine-5-carboxylic acid, benzyl ester;

2-((S)-(1-Oxo-2(R)-pivaloyloxymethylthio-3-phenylpropyl)amino)-hexahydro-3-oxo-1H-pyrazolo[1,2-a]pyridazine-5-carboxylic acid;

2-((S)-(1-Oxo-2(R)-pivaloyloxymethylthio-3-phenylpropyl)amino)-hexahydro-3-oxo-1H-pyrazolo[1,2-a]pyridazine-5-carboxylic acid, benzyl ester;

2-((S)-(1-Oxo-2(R)-acetylthio-3-(3,4-methylenedioxyphenyl)propyl)amino)-hexahydro-3-oxo-1H-pyrazolo[1,2-a]pyridazine-5-carboxylic acid, t-butyl ester;

2-((S)-(1-Oxo-2(R)-acetylthio-3-(3,4-methylenedioxyphenyl)propyl)amino)-hexahydro-3-oxo-1H-pyrazolo[1,2-a]pyridazine-5-carboxylic acid;

2-((S)-(1-Oxo-2(R)-thio-3-(3,4-methylenedioxyphenyl)propyl)amino)-hexahydro-3-oxo-1H-pyrazolo[1,2-a]pyridazine-5-carboxylic acid;

2-((S)-(1-Oxo-2(R)-thio-3-(3,4-methylenedioxyphenyl)propyl)amino)-hexahydro-3-oxo-1H-pyrazolo[1,2-a]pyridazine-5-carboxylic acid, benzyl ester;

2-((S)-(1-Oxo-2(R)-pivaloyloxymethylthio-3-(3,4-methylenedioxyphenyl)propyl)amino)-hexahydro-3-oxo-1H-pyrazolo[1,2-a]pyridazine-5-carboxylic acid;

2-((S)-(1-Oxo-2(R)-pivaloyloxymethylthio-3-(3,4-methylenedioxyphenyl)propyl)amino)-hexahydro-3-oxo-1H-pyrazolo[1,2-a]pyridazine-5-carboxylic acid, benzyl ester;

8-((S)-(1-Oxo-2(R)-acetylthio-3-phenylpropyl)amino)-hexahydro-9-oxopyridazo[1,2-a]pyridazine-1-carboxylic acid, t-butyl ester;

8-((S)-(1-Oxo-2(R)-acetylthio-3-phenylpropyl)amino)-hexahydro-9-oxopyridazo[1,2-a]pyridazine-1-carboxylic acid;

8-((S)-(1-Oxo-2(R)-thio-3-phenylpropyl)amino)-hexahydro-9-oxopyridazo[1,2-a]pyridazine-1-carboxylic acid;

8-((S)-(1-Oxo-2(R)-thio-3-phenylpropyl)amino)-hexahydro-9-oxopyridazo[1,2-a]pyridazine-1-carboxylic acid, benzyl ester;

8-((S)-(1-Oxo-2(R)-pivaloyloxymethylthio-3-phenylpropyl)amino)-hexahydro-9-oxopyridazo[1,2-a]pyridazine-1-carboxylic acid;

8-((S)-(1-Oxo-2(R)-pivaloyloxymethylthio-3-phenylpropyl)amino)-hexahydro-9-oxopyridazo[1,2-a]pyridazine-1-carboxylic acid, benzyl ester;

8-((S)-(1-Oxo-2(R)-acetylthio-3-(3,4-methylenedioxyphenyl)propyl)amino)-hexahydro-9-oxopyridazo[1,2-a]pyridazine-1-carboxylic acid, t-butyl ester;

8-((S)-(1-Oxo-2(R)-acetylthio-3-(3,4-methylenedioxyphenyl)propyl)amino)-hexahydro-9oxopyridazo[1,2-a]pyridazine-1-carboxylic acid;

8-((S)-(1-Oxo-2(R)-thio-3-(3,4-methylenedioxyphenyl)propyl)amino)-hexahydro-9oxopyridazo[1,2-a]pyridazine-1-carboxylic acid;

8-((S)-(1-Oxo-2(R)-thio-3-(3,4-methylenedioxyphenyl)propyl)amino)-hexahydro-9oxopyridazo[1,2-a]pyridazine-1-carboxylic acid, benzyl ester;

8-((S)-(1-Oxo-2(R)-pivaloyloxymethylthio-3-(3,4-methylenedioxyphenyl)propyl)amino)-hexahydro-9oxopyridazo[1,2-a]pyridazine-1-carboxylic acid;

8-((S)-(1-Oxo-2(R)-pivaloyloxymethylthio-3-(3,4-methylenedioxyphenyl)propyl)amino)-hexahydro- 9-oxopyridazo[1,2-a]pyridazine-1-carboxylic acid, benzyl ester;

8-((S)-(1-Oxo-2(R)-acetylthio-3-phenylpropyl)amino)-1,4,6,7,8,9-hexahydro-6,9-dioxopyridazo[1,2-a]pyridazine-1-carboxylic acid, t-butyl ester;

8-((S)-(1-Oxo-2(R)-acetylthio-3-phenylpropyl)amino)-1,4,6,7,8,9-hexahydro-6,9-dioxopyridazo[1,2-a]pyridazine-1-carboxylic acid;

8-((S)-(1-Oxo-2(R)-thio-3-phenylpropyl)amino)-1,4,6,7,8,9-hexahydro-6,9-dioxopyridazo[1,2-a]pyridazine-1-carboxylic acid;

8-((S)-(1-Oxo-2(R)-thio-3-phenylpropyl)amino)-1,4,6,7,8,9-hexahydro-6,9-dioxopyridazo[1,2-a]pyridazine-1-carboxylic acid, benzyl ester;

8-((S)-(1-Oxo-2(R)-pivaloyloxymethylthio-3-phenylpropyl)amino)-1,4,6,7,8,9-hexahydro-6,9-dioxopyridazo[1,2-a]pyridazine-1-carboxylic acid;

8-((S)-(1-Oxo-2(R)-pivaloyloxymethylthio-3-phenylpropyl)amino)-1,4,6,7,8,9-hexahydro-6,9-dioxopyridazo[1,2-a]pyridazine-1-carboxylic acid, benzyl ester;

8-((S)-(1-Oxo-2(R)-acetylthio-3-(3,4-methylenedioxyphenyl)propyl)amino)-1,4,6,7,8,9-hexahydro-6,9-dioxopyridazo[1,2-a]pyridazine-1-carboxylic acid, t-butyl ester;

8-((S)-(1-Oxo-2(R)-acetylthio-3-(3,4-methylenedioxyphenyl)propyl)amino)-1,4,6,7,8,9-hexahydro-6,9-dioxopyridazo[1,2-a]pyridazine-1-carboxylic acid;

8-((S)-(1-Oxo-2(R)-thio-3-(3,4-methylenedioxyphenyl)propyl)amino)-1,4,6,7,8,9-hexahydro-6,9-dioxopyridazo[1,2-a]pyridazine-1-carboxylic acid;

8-((S)-(1-Oxo-2(R)-thio-3-(3,4-methylenedioxyphenyl)propyl)amino)-1,4,6,7,8,9-hexahydro-6,9-dioxopyridazo[1,2-a]pyridazine-1-carboxylic acid, benzyl ester;

8-((S)-(1-Oxo-2(R)-pivaloyloxymethylthio-3-(3,4-methylenedioxyphenyl)propyl)amino)-1,4,6,7,8,9-hexahydro-6,9-dioxopyridazo[1,2-a]pyridazine-1-carboxylic acid;

8-((S)-(1-Oxo-2(R)-pivaloyloxymethylthio-3-(3,4-methylenedioxyphenyl)propyl)amino)-1,4,6,7,8,9-hexahydro-6,9-dioxopyridazo[1,2-a]pyridazine-1-carboxylic acid, benzyl ester;

9-((S)-(1-Oxo-2(R)-acetylthio-3-phenylpropyl)amino)-octahydro-6,10-dioxo-6H-pyridazo[1,2-a][1,2]diazepine-1-carboxylic acid, t-butyl ester;

9-((S)-(1-Oxo-2(R)-acetylthio-3-phenylpropyl)amino)-octahydro-6,10-dioxo-6H-pyridazo[1,2-a][1,2]diazepine-1-carboxylic acid;

9-((S)-(1-Oxo-2(R)-thio-3-phenylpropyl)amino)-octahydro-6,10-dioxo-6H-pyridazo[1,2-a][1,2]diazepine-1-carboxylic acid;

9-((S)-(1-Oxo-2(R)-thio-3-phenylpropyl)amino)-octahydro-6,10-dioxo-6H-pyridazo[1,2-a][1,2]diazepine-1-carboxylic acid, benzyl ester;

9-((S)-(1-Oxo-2(R)-pivaloyloxymethylthio-3-phenylpropyl)amino)-octahydro-6,10-dioxo-6H-pyridazo[1,2-a][1,2]diazepine-1-carboxylic acid;

9-((S)-(1-Oxo-2(R)-pivaloyloxymethylthio-3-phenylpropyl)amino)-octahydro-6,10-dioxo-6H-pyridazo[1,2-a][1,2]diazepine-1-carboxylic acid, benzyl ester;

9-((S)-(1-Oxo-2(R)-acetylthio-3-(3,4-methylenedioxyphenyl)propyl)amino)-octahydro-6,10-dioxo-6H-pyridazo[1,2-a][1,2]diazepine-1-carboxylic acid, t-butyl ester;

9-((S)-(1-Oxo-2(R)-acetylthio-3-(3,4-methylenedioxyphenyl)propyl)amino)-octahydro-6,10-dioxo-6H-pyridazo[1,2-a][1,2]diazepine-1-carboxylic acid;

9-((S)-(1-Oxo-2(R)-thio-3-(3,4-methylenedioxyphenyl)propyl)amino)-octahydro-6,10-dioxo-6H-pyridazo[1,2-a][1,2]diazepine-1-carboxylic acid;

9-((S)-(1-Oxo-2(R)-thio-3-(3,4-methylenedioxyphenyl)propyl)amino)-octahydro-6,10-dioxo-6H-pyridazo[1,2-a][1,2]diazepine-1-carboxylic acid, benzyl ester;

9-((S)-(1-Oxo-2(R)-pivaloyloxymethylthio-3-(3,4-methylenedioxyphenyl)propyl)amino)-octahydro-6,10-dioxo-6H-pyridazo[1,2-a][1,2]diazepine-1-carboxylic acid;

9-((S)-(1-Oxo-2(R)-pivaloyloxymethylthio-3-(3,4-methylenedioxyphenyl)propyl)amino)-octahydro-6,10-dioxo-6H-pyridazo[1,2-a][1,2]diazepine-1-carboxylic acid, benzyl ester;

8-((S)-(1-Oxo-2(S)-acetylthio-3-phenylpropyl)amino)-2,3,6,7,8,9-hexahydro-5,9-dioxo-1H,5H-pyrazolo[1,2-a][1,2]diazepine-1-carboxylic acid, t-butyl ester;

8-((S)-(1-Oxo-2(S)-acetylthio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(S)-thio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(S)-thio-3-phenylpropyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(S)-pivaloyloxymethylthio-3-phenylpropyl)amino)-2,3,6,7,8,9-hexahydro-5,9-dioxo-1H,5H-pyrazolo[1,2-a][1,2]diazepine-1-carboxylic acid;

8-((S)-(1-Oxo-2(S)-pivaloyloxymethylthio-3-phenylpropyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(S)-acetylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid, t-butyl ester;

8-((S)-(1-Oxo-2(S)-acetylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid;

8-((S)-(1-Oxo-2(S)-thio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid;

8-((S)-(1-Oxo-2(S)-thio-3-(3,4-methylenedioxyphenyl)propyl)amino)-2,3,6,7 8,9-hexahydro-5,9-dioxo-1H,5H-pyrazolo[1,2-a][1,2]diazepine-1-carboxylic acid, benzyl ester;

8-((S)-(1-Oxo-2(S)-pivaloyloxymethylthio-3-(3,4-methylenedioxyphenyl)propyl)amino)-2,3,6,7 8,9-hexahydro-5,9-dioxo-1H,5H-pyrazolo[1,2-a][1,2]diazepine-1-carboxylic acid;

8-((S)-(1-Oxo-2(S)-pivaloyloxymethylthio-3-(3,4-methylenedioxyphenyl)propyl)amino)-2,3,6,7,8,9-hexahydro-5,9-dioxo-1H,5H-pyrazolo[1,2-a][1,2]diazepine-1-carboxylic acid, benzyl ester;

8-((S)-(1-Oxo-2(S)-acetylthio-3-phenylpropyl)amino)-octahydro-6,9-dioxopyridazo[1,2-a]pyridazine-1-carboxylic acid, t-butyl ester;

8-((S)-(1-Oxo-2(S)-acetylthio-3-phenylpropyl)amino)-octahydro-6,9-dioxopyridazo[1,2-a]pyridazine-1-carboxylic acid;

8-((S)-(1-Oxo-2(S)-thio-3-phenylpropyl)amino)-octahydro-6,9-dioxopyridazo[1,2-a]pyridazine-1-carboxylic acid;

8-((S)-(1-Oxo-2(S)-thio-3-phenylpropyl)amino)-octahydro-6,9-dioxopyridazo[1,2-a]pyridazine-1-carboxylic acid, benzyl ester;

8-((S)-(1-Oxo-2(S)-pivaloyloxymethylthio-3-phenylpropyl)amino)-octahydro-6,9-dioxopyridazo[1,2-a]pyridazine-1-carboxylic acid;

8-((S)-(1-Oxo-2(S)-pivaloyloxymethylthio-3-phenylpropyl)amino)-octahydro-6,9-dioxopyridazo[1,2-a]pyridazine-1-carboxylic acid, benzyl ester;

8-((S)-(1-Oxo-2(S)-acetylthio-3-(3,4-methylenedioxyphenyl)propyl)amino)-octahydro-6,9dioxopyridazo[1,2-a]pyridazine-1-carboxylic acid, t-butyl ester;

8-((S)-(1-Oxo-2(S)-acetylthio-3-(3,4-methylenedioxyphenyl)propyl)amino)-octahydro-6,9dioxopyridazo[1,2-a]pyridazine-1-carboxylic acid;

8-((S)-(1-Oxo-2(S)-thio-3-(3,4-methylenedioxyphenyl)propyl)amino)-octahydro-6,9dioxopyridazo[1,2-a]pyridazine-i-carboxylic acid;

8-((S)-(1-Oxo-2(S)-thio-3-(3,4-methylenedioxyphenyl)propyl)amino)-octahydro-6,9dioxopyridazo[1,2-a]pyridazine-1-carboxylic acid, benzyl ester;

8-((S)-(1-Oxo-2(S)-pivaloyloxymethylthio-3-(3,4-methylenedioxyphenyl)propyl)amino)-octahydro-6,9dioxopyridazo[1,2-a]pyridazine-1-carboxylic acid;

8-((S)-(1-Oxo-2(S)-pivaloyloxymethylthio-3-(3,4-methylenedioxyphenyl)propyl)amino)-octahydro-6,9dioxopyridazo[1,2-a]pyridazine-1-carboxylic acid, benzyl ester;

8-((S)-(1-Oxo-2(S)-acetylthio-3-phenylpropyl)amino)-octahydro-9-oxopyridazo[1,2-a]pyridazine-1-carboxylic acid, t-butyl ester;

8-((S)-(1-Oxo-2(S)-acetylthio-3-phenylpropyl)amino)-octahydro-9-oxopyridazo[1,2-a]pyridazine-1-carboxylic acid;

8-((S)-(1-Oxo-2(S)-thio-3-phenylpropyl)amino)-octahydro-9-oxopyridazo[1,2-a]pyridazine-1-carboxylic acid;

8-((S)-(1-Oxo-2(S)-thio-3-phenylpropyl)amino)-octahydro-9-oxopyridazo[1,2-a]pyridazine-1-carboxylic acid, benzyl ester;

8-((S)-(1-Oxo-2(S)-pivaloyloxymethylthio-3-phenylpropyl)amino)-octahydro-9-oxopyridazo[1,2-a]pyridazine-1-carboxylic acid;

8-((S)-(1-Oxo-2(S)-pivaloyloxymethylthio-3-phenylpropyl)amino)-octahydro-9-oxopyridazo[1,2-a]pyridazine-1-carboxylic acid, benzyl ester;

8-((S)-(1-Oxo-2(S)-acetylthio-3-(3,4-methylenedioxyphenyl)propyl)amino)-octahydro-9oxopyridazo[1,2-a]pyridazine-1-carboxylic acid, t-butyl ester;

8-((S)-(1-Oxo-2(S)-acetylthio-3-(3,4-methylenedioxyphenyl)propyl)amino)-octahydro-9oxopyridazo[1,2-a]pyridazine-1-carboxylic acid;

8-((S)-(1-Oxo-2(S)-thio-3-(3,4-methylenedioxyphenyl)propyl)amino)-octahydro-9oxopyridazo[1,2-a]pyridazine-1-carboxylic acid;

8-((S)-(1-Oxo-2(S)-thio-3,(3,4-methylenedioxyphenyl)propyl)amino)-octahydro-9oxopyridazo[1,2-a]pyridazine-1-carboxylic acid, benzyl ester;

8-((S)-(1-Oxo-2(S)-pivaloyloxymethylthio-3-(3,4-methylenedioxyphenyl)propyl)amino)-octahydro-9oxopyridazo[1,2-a]pyridazine-1-carboxylic acid;

8-((S)-(1-Oxo-2(S)-pivaloyloxymethylthio-3-(3,4-methylenedioxyphenyl)propyl)amino)-octahydro-9oxopyridazo[1,2-a]pyridazine-1-carboxylic acid, benzyl ester;

8-((S)-(1-Oxo-2(S)-acetylthio-3-phenylpropyl)amino)-1,4,5,7,8,9-hexahydro-6,9-dioxopyridazo[1,2-a]pyridazine-1-carboxylic acid, t-butyl ester;

8-((S)-(1-Oxo-2(S)-acetylthio-3-phenylpropyl)amino)-1,4,5,7,8,9-hexahydro-6,9-dioxopyridazo[1,2-a]pyridazine-1-carboxylic acid;

8-((S)-(1-Oxo-2(S)-thio-3-phenylpropyl)amino)-1,4,5,7,8,9-hexahydro-6,9-dioxopyridazo[1,2-a]pyridazine-1-carboxylic acid;

8-((S)-(1-Oxo-2(S)-thio-3-phenylpropyl)amino)-1,4,5,7,8,9-hexahydro-6,9-dioxopyridazo[1,2-a]pyridazine-1-carboxylic acid, benzyl ester;

8-((S)-(1-Oxo-2(S)-pivaloyloxymethylthio-3-phenylpropyl)amino)-1,4,5,7,8,9-hexahydro-6,9dioxopyridazo[1,2-a]pyridazine-1-carboxylic acid;

8-((S)-(1-Oxo-2(S)-pivaloyloxymethylthio-3-phenylpropyl)amino)-1,4,5,7,8,9-hexahydro-6,9dioxopyridazo[1,2-a]pyridazine-1-carboxylic acid, benzyl ester;

8-((S)-(1-Oxo-2(S)-acetylthio-3-(3,4-methylenedioxyphenyl)propyl)amino)-1,4,5,7,8,9-hexahydro-6,9-dioxopyridazo[1,2-a]pyridazine-1-carboxylic acid, t-butyl ester;

8-((S)-(1-Oxo-2(S)-acetylthio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(S)-thio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(S)-thio-3-(3,4-methylenedioxyphenyl)propyl)amino)-1,4,5,7,8,9-hexahydro-6,9-dioxopyridazo[1,2-a]pyridazine-1-carboxylic acid, benzyl ester;

8-((S)-(1-Oxo-2(S)-pivaloyloxymethylthio-3-(3,4-methylenedioxyphenyl)propyl)amino)-1,4,5,7,8,9-hexahydro-6,9-dioxopyridazo[1,2-a]pyridazine-1-carboxylic acid;

8-((S)-(1-Oxo-2(S)-pivaloyloxymethylthio-3-(3,4-methylenedioxyphenyl)propyl)amino)-1,4,5,7,8,9-hexahydro-6,9-dioxopyridazo[1,2-a]pyridazine-1-carboxylic acid, benzyl ester;

2-((S)-(1-Oxo-2(S)-acetylthio-3-phenylpropyl)amino)-hexahydro-3-oxo-1H-pyrazolo[1,2-a]pyridazine-5-carboxylic acid, t-butyl ester;

2-((S)-(1-Oxo-2(S)-acetylthio-3-phenylpropyl)amino)-hexahydro-3-oxo-1H-pyrazolo[1,2-a]pyridazine-5-carboxylic acid;

2-((S)-(1-Oxo-2(S)-thio-3-phenylpropyl)amino)-hexahydro-3-oxo-1H-pyrazolo[1,2-a]pyridazine-5-carboxylic acid;

2-((S)-(1-Oxo-2(S)-thio-3-phenylpropyl)amino)-hexahydro-3-oxo-1H-pyrazolo[1,2-a]pyridazine-5-carboxylic acid, benzyl ester;

2-((S)-(1-Oxo-2(S)-pivaloyloxymethylthio-3-phenylpropyl)amino)-hexahydro-3-oxo-1H-pyrazolo[1,2-a]pyridazine-5-carboxylic acid;

2-((S)-(1-Oxo-2(S)-pivaloyloxymethylthio-3-phenylpropyl)amino)-hexahydro-3-oxo-1H-pyrazolo[1,2-a]pyridazine-5-carboxylic acid, benzyl ester;

2-((S)-(1-Oxo-2(S)-acetylthio-3-(3,4-methylenedioxyphenyl)propyl)amino)-hexahydro-3-oxo-1H-pyrazolo[1,2-a]pyridazine-5-carboxylic acid, t-butyl ester;

2-((S)-(1-Oxo-2(S)-acetylthio-3-(3,4-methylenedioxyphenyl)propyl)amino)-hexahydro-3-oxo-1H-pyrazolo[1,2-a]pyridazine-5-carboxylic acid;

2-((S)-(1-Oxo-2(S)-thio-3-(3,4-methylenedioxyphenyl)-propyl)amino)-hexahydro-3-oxo-1H-pyrazolo[1,2-a]pyridazine-5-carboxylic acid;

2-((S)-(1-Oxo-2(S)-thio-3-(3,4-methylenedioxyphenyl)-propyl)amino)-hexahydro-3-oxo-1H-pyrazolo[1,2-a]pyridazine-5-carboxylic acid, benzyl ester;

2-((S)-(1-Oxo-2(S)-pivaloyloxymethylthio-3-(3,4-methylenedioxyphenyl)propyl)amino)-hexahydro-3-oxo-1H-pyrazolo[1,2-a]pyridazine-5-carboxylic acid;

2-((S)-(1-Oxo-2(S)-pivaloyloxymethylthio-3-(3,4-methylenedioxyphenyl)propyl)amino)-hexahydro-3-oxo-1H-pyrazolo[1,2-a]pyridazine-5-carboxylic acid, benzyl ester;

8-((S)-(1-Oxo-2(S)-acetylthio-3-phenylpropyl)amino)-octahydro-9-oxopyridazo[1,2-a]pyridazine-1-carboxylic acid, t-butyl ester;

8-((S)-(1-Oxo-2(S)-acetylthio-3-phenylpropyl)amino)-octahydro-9-oxopyridazo[1,2-a]pyridazine-1-carboxylic acid;

8-((S)-(1-Oxo-2(S)-thio-3-phenylpropyl)amino)-octahydro-9-oxopyridazo[1,2-a]pyridazine-1-carboxylic acid;

8-((S)-(1-Oxo-2(S)-thio-3-phenylpropyl)amino)-octahydro-9-oxopyridazo[1,2-a]pyridazine-1-carboxylic acid, benzyl ester;

8-((S)-(1-Oxo-2(S)-pivaloyloxymethylthio-3-phenylpropyl)amino)-octahydro-9-oxopyridazo[1,2-a]pyridazine-1-carboxylic acid;

8-((S)-(1-Oxo-2(S)-pivaloyloxymethylthio-3-phenylpropyl)amino)-octahydro-9-oxopyridazo[1,2-a]pyridazine-1-carboxylic acid, benzyl ester;

8-((S)-(1-Oxo-2(S)-acetylthio-3-(3,4-methylenedioxyphenyl)propyl)amino)-octahydro-9oxopyridazo[1,2-a]pyridazine-1-carboxylic acid, t-butyl ester;

8-((S)-(1-Oxo-2(S)-acetylthio-3-(3,4-methylenedioxyphenyl)propyl)amino)-octahydro-9oxopyridazo[1,2-a]pyridazine-1-carboxylic acid;

8-((S)-(1-Oxo-2(S)-thio-3-(3,4-methylenedioxyphenyl)-propyl)amino)-octahydro-9oxopyridazo[1,2-a]pyridazine-1-carboxylic acid;

8-((S)-(1-Oxo-2(S)-thio-3-(3,4-methylenedioxyphenyl)-propyl)amino)-octahydro-9oxopyridazo[1,2-a]pyridazine-1-carboxylic acid, benzyl ester;

8-((S)-(1-Oxo-2(S)-pivaloyloxymethylthio-3-(3,4-methylenedioxyphenyl)propyl)amino)-octahydro-9oxopyridazo[1,2-a]pyridazine-1-carboxylic acid;

8-((S)-(1-Oxo-2(S)-pivaloyloxymethylthio-3-(3,4-methylenedioxyphenyl)propyl)amino)-octahydro-9oxopyridazo[1,2-a]pyridazine-1-carboxylic acid, benzyl ester;

8-((S)-(1-Oxo-2(S)-acetylthio-3-phenylpropyl)amino)-1,4,6,7,8,9-hexahydro-6,9-dioxopyridazo[1,2-a]pyridazine-1-carboxylic acid, t-butyl ester;

8-((S)-(1-Oxo-2(S)-acetylthio-3-phenylpropyl)amino)-1,4,6,7,8,9-hexahydro-6,9-dioxopyridazo[1,2-a]pyridazine-1-carboxylic acid;

8-((S)-(1-Oxo-2(S)-thio-3-phenylpropyl)amino)-1,4,6,7,8,9-hexahydro-6,9-dioxopyridazo[1,2-a]pyridazine-1-carboxylic acid;

8-((S)-(1-Oxo-2(S)-thio-3-phenylpropyl)amino)-1,4,6,7,8,9-hexahydro-6,9-dioxopyridazo[1,2-a]pyridazine-1-carboxylic acid, benzyl ester;

8-((S)-(1-Oxo-2(S)-pivaloyloxymethylthio-3-phenylpropyl)amino)-1,4,6,7,8,9-hexahydro-6,9-dioxopyridazo[1,2-a]pyridazine-1-carboxylic acid;

8-((S)-(1-Oxo-2(S)-pivaloyloxymethylthio-3-phenylpropyl)amino)-1,4,6,7,8,9-hexahydro-6,9dioxopyridazo[1,2-a]pyridazine-1-carboxylic acid, benzyl ester;

8-((S)-(1-Oxo-2(S)-acetylthio-3-(3,4-methylenedioxyphenyl)propyl)amino)-1,4,6,7,8,9-hexahydro-6,9-dioxopyridazo[1,2-a]pyridazine-1-carboxylic acid, t-butyl ester;

8-((S)-(1-Oxo-2(S)-acetylthio-3-(3,4-methylenedioxyphenyl)propyl)amino)-1,4,6,7,8,9-hexahydro-6,9-dioxopyridazo[1,2-a]pyridazine-1-carboxylic acid;

8-((S)-(1-Oxo-2(S)-thio-3-(3,4-methylenedioxyphenyl)-propyl)amino)-1,4,6,7,8,9-hexahydro-6,9-dioxopyridazo[1,2-a]pyridazine-1-carboxylic acid;

8-((S)-(1-Oxo-2(S)-thio-3-(3,4-methylenedioxyphenyl)-propyl)amino)-1,4,6,7,8,9-hexahydro-6,9-dioxopyridazo[1,2-a]pyridazine-1-carboxylic acid, benzyl ester;

8-((S)-(1-Oxo-2(S)-pivaloyloxymethylthio-3-(3,4-methylenedioxyphenyl)propyl)amino)-1,4,6,7,8,9-hexahydro-6,9-dioxopyridazo[1,2-a]pyridazine-1-carboxylic acid;

8-((S)-(1-Oxo-2(S)-pivaloyloxymethylthio-3-(3,4-methylenedioxyphenyl)propyl)amino)-1,4,6,7,8,9-hexahydro-6,9-dioxopyridazo[1,2-a]pyridazine-1-carboxylic acid, benzyl ester;

9-((S)-(1-Oxo-2(S)-thio-3-phenylpropyl)amino)-octahydro-6,10-dioxo-6H-pyridazo[1,2-a][1,2]diazepine-1-carboxylic acid, benzyl ester;

9-((S)-(1-Oxo-2(S)-pivaloyloxymethylthio-3-phenylpropyl)amino)-octahydro-6,10-dioxo-6H-pyridazo[1,2-a][1,2]diazepine-1-carboxylic acid;

9-((S)-(1-Oxo-2(S)-pivaloyloxymethylthio-3-phenylpropyl)amino)-octahydro-6,10-dioxo-6H-pyridazo[1,2-a][1,2]diazepine-1-carboxylic acid, benzyl ester;

9-((S)-(1-Oxo-2(R)-acetylthio-3-phenylpropyl)amino)-octahydro-10-oxo-6H-pyridazo[1,2-a][1,2]diazepine-1-carboxylic acid, t-butyl ester;

9-((S)-(1-Oxo-2(R)-acetylthio-3-phenylpropyl)amino)-octahydro-10-oxo-6H-pyridazo[1,2-a][1,2]diazepine-1-carboxylic acid;

9-((S)-(1-Oxo-2(R)-thio-3-phenylpropyl)amino)-octahydro-10-oxo-6H-pyridazo[1,2-a][1,2]diazepine-1-carboxylic acid;

9-((S)-(1-Oxo-2(R)-thio-3-phenylpropyl)amino)-octahydro-10-oxo-6H-pyridazo[1,2-a][1,2]diazepine-1-carboxylic acid, benzyl ester;

9-((S)-(1-Oxo-2(R)-pivaloyloxymethylthio-3-phenylpropyl)amino)-octahydro-10-oxo-6H-pyridazo[1,2-a][1,2]diazepine-1-carboxylic acid;

9-((S)-(1-Oxo-2(R)-pivaloyloxymethylthio-3-phenylpropyl)amino)-octahydro-10-oxo-6H-pyridazo[1,2-a][1,2]diazepine-1-carboxylic acid, benzyl ester;

9-((S)-(1-Oxo-2(R)-acetylthio-3-(3,4-methylenedioxyphenyl)propyl)amino)-octahydro-10-oxo-6H-pyridazo[1,2-a][1,2]diazepine-1-carboxylic acid, t-butyl ester;

9-((S)-(1-Oxo-2(R)-acetylthio-3-(3,4-methylenedioxyphenyl)propyl)amino)-octahydro-10-oxo-6H-pyridazo[1,2-a][1,2]diazepine-1-carboxylic acid;

9-((S)-(1-Oxo-2(R)-thio-3-(3,4-methylenedioxyphenyl)-propyl)amino)-octahydro-10-oxo-6H-pyridazo[1,2-a][1,2]diazepine-1-carboxylic acid;

9-((S)-(1-Oxo-2(R)-thio-3-(3,4-methylenedioxyphenyl)-propyl)amino)-octahydro-10-oxo-6H-pyridazo[1,2-a][1,2]diazepine-1-carboxylic acid, benzyl ester;

9-((S)-(1-Oxo-2(R)-pivaloyloxymethylthio-3-(3,4-methylenedioxyphenyl)propyl)amino)-octahydro-10- oxo-6H-pyridazo[1,2-a][1,2]diazepine-1-carboxylic acid;

9-((S)-(1-Oxo-2(R)-pivaloyloxymethylthio-3-(3,4-methylenedioxyphenyl)propyl)amino)-octahydro-10-oxo-6H- pyridazo[ 1,2-a][1,2]diazepine-1-carboxylic acid, benzyl ester;

9-((S)-(1-Oxo-2(S)-acetylthio-3-(3,4-methylenedioxyphenyl)propyl)amino)-octahydro-10-oxo-6H-pyridazo[1,2-a][1,2]diazepine-1-carboxylic acid, t-butyl ester;

9-((S)-(1-Oxo-2(S)-acetylthio-3-(3,4-methylenedioxyphenyl)propyl)amino)-octahydro-10-oxo-6H-pyridazo[1,2-a][1,2]diazepine-1-carboxylic acid;

9-((S)-(1-Oxo-2(S)-thio-3-(3,4-methylenedioxyphenyl)-propyl)amino)-octahydro-10-oxo-6H-pyridazo[1,2-a][1,2]diazepine-1-carboxylic acid;

9-((S)-(1-Oxo-2(S)-thio-3-(3,4-methylenedioxyphenyl)-propyl)amino)-octahydro-10-oxo-6H-pyridazo[1,2-a][1,2]diazepine-1-carboxylic acid, benzyl ester;

9-((S)-(1-Oxo-2(S)-pivaloyloxymethylthio-3-(3,4-methylenedioxyphenyl)propyl)amino)-octahydro-10-oxo-6H-pyridazo[1,2-a][1,2]diazepine-1-carboxylic acid;

9-((S)-(1-Oxo-2(S)-pivaloyloxymethylthio-3-(3,4-methylenedioxyphenyl)propyl)amino)-octahydro-10-oxo-6H-pyridazo[1,2-a][1,2]diazepine-1-carboxylic acid, benzyl ester;

9-((S)-(1-Oxo-2(S)-acetylthio-3-(3,4-methylenedioxyphenyl)propyl)amino)-octahydro-6,10-dioxo-6H-pyridazo[1,2-a][1,2]diazepine-1-carboxylic acid, t-butyl ester;

9-((S)-(1-Oxo-2(S)-acetylthio-3-(3,4-methylenedioxyphenyl)propyl)amino)-octahydro-6,10-dioxo-6H-pyridazo[1,2-a][1,2]diazepine-1-carboxylic acid;

9-((S)-(1-Oxo-2(S)-thio-3-(3,4-methylenedioxyphenyl)-propyl)amino)-octahydro-6,10-dioxo-6H-pyridazo[1,2-a][1,2]diazepine-1-carboxylic acid;

9-((S)-(1-Oxo-2(S)-thio-3-(3,4-methylenedioxyphenyl)-propyl)amino)-octahydro-6,10-dioxo-6H-pyridazo[1,2-a][1,2]diazepine-1-carboxylic acid, benzyl ester;

9-((S)-(1-Oxo-2(S)-pivaloyloxymethylthio-3-(3,4-methylenedioxyphenyl)propyl)amino)-octahydro-6,10-dioxo-6H-pyridazo[1,2-a][1,2]diazepine-1-carboxylic acid;

9-((S)-(1-Oxo-2(S)-pivaloyloxymethylthio-3-(3,4-methylenedioxyphenyl)propyl)amino)-octahydro-6,10-dioxo-6H-pyridazo[1,2-a][1,2]diazepine-1-carboxylic acid, benzyl ester.

In a further embodiment, the present invention provides a method of inhibiting enkephalinase in a patient in need thereof comprising administering to said patient an effective enkephalinase inhibitory amount of a compound of Formula (I).

As used herein, the term "patient" refers to warmblooded animals or mammals, including mice, rats and humans. A patient is in need of treatment to inhibit enkephalinase when the patient is suffering from acute or chronic pain and is in need of an endorphin- or enkephalin-mediated analgesic effect. In addition, a patient is in need of treatment to inhibit enkephalinase when the patient is suffering from a disease state characterized by abnormalities in fluid, electrolyte, blood pressure, intraocular pressure, renin, or aldosterone homeostasis, such as, but not limited to, hypertension, renal diseases, hyperaldosteronemia, cardiac hypertrophy, glaucoma and congestive heart failure. In these instances the patient is in need of an ANP-mediated diuretic, natriuretic, hypotensive, hypoaldosteronemic effect. Inhibition of enkephalinase would provide an endorphin- or enkephalin-mediated analgesic effect by inhibiting the metabolic degradation of endorphins and enkephalins. Inhibition of enkephalinase would provide an ANP-mediated diuretic, natriuretic, hypotensive, hypoaldosteronemic effect by inhibiting the metabolic degradation of ANP. Inhibition of enkephalinase would also potentiate endogenous levels of bradykinin. Inhibition of enkephalinase would also modulate intestinal smooth muscle contractility and would be useful in the treatment of irritable bowel syndrome.

In addition, a patient is in need of treatment to inhibit enkephalinase when the patient is in need of an antidepressant effect or a reduction in severity of withdrawal symptoms associated with termination of opiate or morphine administration.

The identification of those patients who are in need of treatment to inhibit enkephalinase is well within the ability and knowledge of one skilled in the art. A clinician skilled in the art can readily identify, by the use of clinical tests, physical examination and medical/family history, those patients who are in need of an endorphin- or enkephalin-mediated analgesic effect or who are in need of an ANP-mediated diuretic, natriuretic, hypotensive or hypoaldosteronemic effect.

An effective enkephalinase inhibitory amount of a compound of Formula (I) is an amount which is effective in inhibiting enkephalinase and in thus inhibiting the metabolic degradation of the naturally-occurring circulating regulatory peptides such as the endorphins, including enkephalins, and ANP. Successful treatment is also understood to include prophylaxis in treating a patient in those instances such as, for example, in a pre-operative procedure, where a patient will be suffering from acute or chronic pain in the near future.

An effective enkephalinase inhibitory amount of a compound of Formula (I) is an amount which is effective in inhibiting enkephalinase in a patient in need thereof which results, for example, in endorphin- or enkephalin-mediated analgesic effects or in ANP-mediated diuretic, natriuretic, hypotensive, hypoaldosteronemic effect.

An effective enkephalinase inhibitory dose can be readily determined by the use of conventional techniques and by observing results obtained under analogous circumstances. In determining the effective dose, a number of factors are considered including, but not limited to: the species of patient; its size, age, and general health; the specific disease involved; the degree of or involvement or the severity of the disease; the response of the individual patient; the particular compound administered; the mode of administration; the bioavailability characteristics of the preparation administered; the dose regimen selected; and the use of concomitant medication.

An effective enkephalinase inhibitory amount of a compound of Formula (I) will generally vary from about 0.01 milligram per kilogram of body weight per day (mg/kg/day) to about 20 mg/kg/day. A daily dose of from about 0.1 mg/kg to about 10 mg/kg is preferred.

In addition, the present invention further provides a method of inhibiting ACE in a patient in need thereof comprising administering to said patient an effective ACE inhibitory amount of a compound of Formula (I). A patient is in need of treatment to inhibit ACE when the patient is suffering from hypertension, chronic congestive heart failure, hyperaldosteronemia or cognitive disorders. Inhibition of ACE reduces levels of angiotensin II and thus inhibits the vasopressor, hypertensive and hyperaldosteronemic effects caused thereby. An effective ACE inhibitory amount of a compound of Formula (I) is that amount which is effective in inhibiting ACE in a patient in need thereof which results, for example, in a hypotensive effect. An effective ACE inhibitory amount and an effective ACE inhibitory dose are the same as that described above for an effective enkephalinase inhibitory amount and dose.

In addition, the present invention further provides a method for treating a patient suffering from smooth cell proliferation. An effective smooth cell proliferation inhibitory amount of a compound of Formula (I) is that amount which is effective in inhibiting smooth cell proliferation in a patient in need thereof which results, for example, in a reduced myointimal thickening after vascular injury. An effective smooth cell proliferation inhibitory amount and an effective smooth cell proliferation inhibitory dose are the same as that described above for an effective enkephalinase inhibitory amount and dose.

In effecting treatment of a patient, compounds of Formula (I) can be administered in any form or mode which makes the compound bioavailable in effective amounts, including oral and parenteral routes. For example, the compound can be administered orally, subcutaneously, intramuscularly, intravenously, transdermally, intranasally, rectally, and the like. Oral administration is generally preferred. One skilled in the art of preparing Formulations can readily select the proper form and mode of administration depending upon the disease state to be treated, the stage of the disease, and other relevant circumstances.

Compounds of Formula (I) can be administered in the form of pharmaceutical compositions or medicaments which are made by combining the compounds of Formula (I) with pharmaceutically acceptable carriers or excipients, the proportion and nature of which are determined by the chosen route of administration, and standard pharmaceutical practice.

In another embodiment, the present invention provides compositions comprising a compound of Formula (I) in admixture or otherwise in association with one or more inert carriers. These compositions are useful, for example, as assay standards, as convenient means of making bulk shipments, or as pharmaceutical compositions. An assayable amount of a compound of Formula (I) is an amount which is readily measurable by standard assay procedures and techniques as are well known and appreciated by those skilled in the art. Assayable amounts of a compound of Formula (I) will generally vary from about 0,001% to about 75% of the composition by weight. Inert carriers can be any material which does not degrade or otherwise covalently react with a compound of Formula (I). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective amount of a compound of Formula (I) in admixture or otherwise in association with one or more pharmaceutically acceptable carriers or excipients.

The pharmaceutical compositions or medicaments are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use and may be administered to the patient in the form of tablets, capsules, suppositories, solution, suspensions, or the like.

The pharmaceutical compositions may be administered orally, for example, with an inert diluent or with an edible carrier. They may be enclosed in gelatin capsules or compressed into tablets. For the purpose of oral therapeutic administration, the compounds of Formula (I) may be incorporated with excipients and used in the form of tablets, troches, capsules, elixirs, suspensions, syrups, wafers, chewing gums and the like. These preparations should contain at least 4% of the compound of Formula (I), the active ingredient, but may be varied depending upon the particular form and may conveniently be between 4% to about 70% of the weight of the unit. The amount of the active ingredient present in compositions is such that a unit dosage form suitable for administration will be obtained.

The tablets, pills, capsules, troches and the like may also contain one or more of the following adjuvants: binders, such as microcrystalline cellulose, gum tragacanth or gelatin; excipients, such as starch or lactose, disintegrating agents such as alginic acid, Primogel, corn starch and the like; lubricants, such as magnesium stearate or Sterotex; glidants, such as colloidal silicon dioxide; and sweetening agents, such as sucrose or saccharin may be added or flavoring agents, such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active ingredient, sucrose as a sweetening agent and certain preservatives, dyes and colorings and flavors. Materials used in preparing these various compositions should be pharmaceutically pure and non-toxic in the amounts used.

For the purpose of parenteral administration, the compounds of Formula (I) may be incorporated into a solution or suspension. These preparations should contain at least 0.1% of a compound of the invention, but may be varied to be between 0.1 and about 50% of the weight thereof. The amount of the active ingredient present in such compositions is such that a suitable dosage will be obtained.

The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of toxicity such as sodium chloride or dextrose. The parenteral preparation can be enclosed in ampules, disposable syringes or multiple dose vials made of glass or plastic.

As with any group of structurally related compounds which possess a particular generic utility, certain groups and configurations are preferred for compounds of Formula (I) in their end-use application.

The compounds of Formula (I) wherein n=2 and B=ethylene are preferred.

It is, of course, understood that the compounds of Formula (I) may exist in a variety of isomeric configurations including structural as well as stereo isomers. It is further understood that the present invention encompasses those compounds of Formula (I) in each of their various structural and stereo isomeric configurations as individual isomers and as mixtures of isomers.

The following specific compounds of Formula (1) are particularly preferred in the end-use application of the compounds of the present invention:

9-[(S)-(1-Oxo-2(R)-acetylthio-3-phenylpropyl)amino]-octahydro-10-oxo-6H-pyridazo[1,2-a][1,2]diazepine-1(S)carboxylic acid;

9-[(S)-(1-Oxo-2(R)-thio-3-phenylpropyl)amino]-octahydro-10-oxo-6H-pyridazo[1,2-a][1,2]diazepine-1(S)-carboxylic acid;

9-[(S)-(1-Oxo-2(S)-acetylthio-3-phenylpropyl)amino]-octahydro-10-oxo-6H-pyridazo[1,2-a][1,2]diazepine-1(S)carboxylic acid;

9-[(S)-(1-Oxo-2(S)-thio-3-phenylpropyl)amino]-octahydro-10-oxo-6H-pyridazo[1,2-a][1,2]diazepine-1(S)-carboxylic acid;

9-[(S)-(1-Oxo-2(S)-acetylthio-3-phenylpropyl)amino]-octahydro-10-oxo-6H-pyridazo[1,2-a][1,2]diazepine-1(S)carboxylic acid, t-butyl ester;

9-[(S)-(1-Oxo-2(S)-thio-3-phenylpropyl)amino]-octahydro-10-oxo-6H-pyridazo[1,2-a][1,2]diazepine-1(S)-carboxylic acid, t-butyl ester;

9-[(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester;

9-[(S)-(1-Oxo-2(S)-thio-3-phenylpropyl)amino]-octahydro-10-oxo-6H-pyridazo[1,2-a][1,2]diazepine-1(R)-carboxylic acid, t-butyl ester;

9-[(S)-(1-Oxo-2(S)-acetylthio-3-phenylpropyl)amino]-octahydro-10-oxo-6H-pyridazo[1,2-a][1,2]diazepine-1(R)-carboxylic acid;

9-[(S)-(1-Oxo-2(S)-thio-3-phenylpropyl)amino]-octahydro-10-oxo-6H-pyridazo[1,2-a][1,2]diazepine-1(R)-carboxylic acid;

9-((S)-(1-Oxo-2(S)-acetylthio-3-phenylpropyl)amino)-octahydro-6,10-dioxo-6H-pyridazo[1,2-a][1,2]diazepine-1(S)-carboxylic acid, t-butyl ester;

9-((S)-(1-Oxo-2(S)-acetylthio-3-phenylpropyl)amino)-octahydro-6,10-dioxo-6H-pyridazo[1,2-a][1,2]diazepine-1(S)-carboxylic acid;

9-((S)-(1-Oxo-2(S)-thio-3-phenylpropyl)amino)-octahydro-6,10-dioxo-6H-pyridazo[1,2-a][1,2]diazepine-1(S)-carboxylic acid; and 9-((S)-(1-Oxo-2(S)-thio-3-phenylpropyl)amino)-octahydro-6,10-dioxo-6H-pyridazo[1,2-a][1,2]diazepine-1(S)-carboxylic acid, t-butyl ester.

The following studies illustrate the utility of the compounds of the present invention as enkephalinase inhibitors and as ACE inhibitors.

Enkephalinase is partially purified from rat kidney. The enzyme is extracted from the microvilli fraction by using Triton X-100 according to the method of Malfroy and Schwartz [J. Biol. Chem. 259, 14365–14370 (1984)] or by using a proteolytic treatment according to the method of Almenoff and Orlowski [Biochem. 22, 590–599 (1983)]. The enzyme is further purified by anion exchange chromatography (Mono Q ™ column, Pharmacia) using a Pharmacia FPLC system. The enzyme activity may be measured by the fluorometric methods of Florentin et al. [Anal. Biochem. 141, 62–69 (1984)] or of Almenoff and Orlowski [J. Neurochemistry 42, 151–157 (1984)]. The enzyme is assayed in 50 mM HEPES buffer (pH 7.4) in a 3.0 mL reaction volume containing 12 μM of the substrate dansyl-D-AlaGly(p-nitro)PheGly ($K_m$=40 μM) at 25° C. The substrate (and inhibitor) is added from a concentrated stock solution in DMSO (up to 0.1 mL DMSO final volume). The enzyme in a small volume (approximately 0.1 μg of FPLC purified protein) is added to initiate the reaction and the rate of fluorescence increase is recorded continuously using a fluorometer (excitation at 339 nm, emission at 562 nm).

The enzymatic activity of ACE is monitored using the spectrophotometric substrate described by Holmquist et al. [Anal. Biochem. 95, 540–548 (1979)] and the buffer system described by Ryan [Methods of Enzymatic Analysis, 3rd ed., H. U. Bergmeyer, editor; vol. V, Verlag Chemie, Weinheim, 1983, pp. 20–34].

What is claimed is:

1. A compound of the Formula

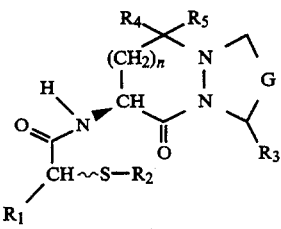

wherein

G represents a methylene, ethylene or vinylene group;

$R_1$ represents a hydrogen, $C_1$-$C_8$ alkyl, —CH$_2$OCH$_2$CH$_2$OCH$_3$ or an Ar—Y— group wherein Ar is a phenyl or naphthyl group unsubstituted or substituted with from one to three substitutents selected from the gorup consisting of methylenedioxy, hydroxy, $C_1$-$C_4$ alkoxy, amino, nitro, fluoro and chloro and Y is a saturated straight or branched chain hydrocarbyl radical of zero to four carbon atoms;

$R_2$ represents a hydrogen, acetyl, —CH$_2$O—C(O)C(CH$_3$)$_3$ or benzoyl;

$R_3$ represents a carboxyl, alkoxycarbonyl or an Ar—Y—O carbonyl group;

$R_4$ and $R_5$ each represent a hydrogen atom or $R_4$ and $R_5$ together represent an oxo group;

n stands for zero, 1 or 2, and pharmaceutically acceptable salts and individual optical isomers thereof.

2. A compound according to claim 1 wherein n=2.

3. A compound according to claim 2 wherein G is an ethylene group.

4. A compound according to claim 3 wherein $R_1$ is phenylmethyl.

5. A method of inhibiting enkephalinase in a patient in need thereof comprising administering to said patient an effective enkephalinase inhibitory amount of a compound of the Formula

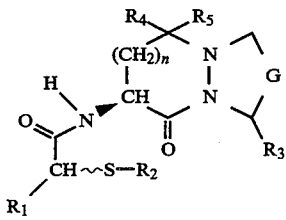

wherein

G represents a methylene, ethylene or vinylene group;

R$_1$ represents a hydrogen, C$_1$-C$_8$ alkyl, —CH$_2$OCH$_2$CH$_2$OCH$_3$ or an Ar—Y— group wherein Ar is a phenyl or naphthyl group unsubstituted or substituted with from one to three substitutents selected from the gorup consisting of methylenedioxy, hydroxy, C$_1$-C$_4$ alkoxy, amino, nitro, fluoro and chloro and Y is a saturated straight or branched chain hydrocarbyl radical of zero to four carbon atoms;

R$_2$ represents a hydrogen, acetyl, —CH$_2$O—C(O)C(CH$_3$)$_3$ or benzoyl;

R$_3$ represents a carboxyl, alkoxycarbonyl or an Ar—Y—O carbonyl group;

R$_4$ and R$_5$ each represent a hydrogen atom or R$_4$ and R$_5$ together represent an oxo group;

n stands for zero, 1 or 2, and pharmaceutically acceptable salts and individual optical isomers thereof.

6. A method according to claim 5 wherein the patient is in need of an endorphin- or enkephalin-mediated analgesic effect.

7. A method according to claim 5 wherein the patient is in need of an ANP-mediated hypotensive effect.

8. A method according to claim 5 wherein the patient is in need of an ANP-mediated diuretic effect.

9. A method according to claim 5 wherein the patient is suffering from congestive heart failure.

10. A method according to claim 5 wherein the patient is suffering from irritable bowel syndrome.

11. A method of inhibiting ACE in a patient in need thereof comprising administering to said patient an effective ACE inhibitory amount of a compound of the Formula

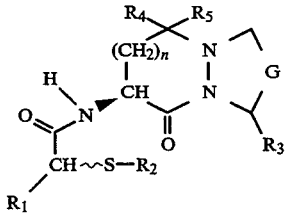

wherein

G represents a methylene, ethylene or vinylene group;

R$_1$ represents a hydrogen, C$_1$-C$_8$ alkyl, —CH$_2$OCH$_2$CH$_2$OCH$_3$ or an Ar—Y— group wherein Ar is a phenyl or naphthyl group unsubstituted or substituted with from one to three substitutents selected from the gorup consisting of methylenedioxy, hydroxy, C$_1$-C$_4$ alkoxy, amino, nitro, fluoro and chloro and Y is a saturated straight or branched chain hydrocarbyl radical of zero to four carbon atoms;

R$_2$ represents a hydrogen, acetyl, —CH$_2$O—C(O)C(CH$_3$)$_3$ or benzoyl;

R$_3$ represents a carboxyl, alkoxycarbonyl or an Ar—Y—O carbonyl group;

R$_4$ and R$_5$ each represent a hydrogen atom or R$_4$ and R$_5$ together represent an oxo group;

n stands for zero, 1 or 2, and pharmaceutically acceptable salts and individual optical isomers thereof.

12. A method according to claim 11 wherein the patient is in need of a hypotensive effect.

13. A method according to claim 11 wherein the patient is in need of a cognition enhancing effect.

14. A method according to claim 11 wherein the patient is suffering from congestive heart failure.

15. A method of inhibiting smooth cell proliferation in a patient in need thereof comprising administering to said patient an effective smooth cell proliferation inhibitory amount of a compound of the formula

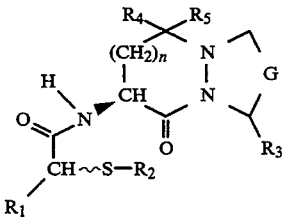

wherein

G represents a methylene, ethylene or vinylene group;

R$_1$ represents a hydrogen, C$_1$-C$_8$ alkyl, —CH$_2$OCH$_2$CH$_2$OCH$_3$ or an Ar—Y— group wherein Ar is a phenyl or naphthyl group unsubstituted or substituted with from one to three substitutents selected from the gorup consisting of methylenedioxy, hydroxy, C$_1$-C$_4$ alkoxy, amino, nitro, fluoro and chloro and Y is a saturated straight or branched chain hydrocarbyl radical of zero to four carbon atoms;

R$_2$ represents a hydrogen, acetyl, —CH$_2$O—C(O)C(CH$_3$)$_3$ or benzoyl;

R$_3$ represents a carboxyl, alkoxycarbonyl or an Ar—Y—O carbonyl group;

R$_4$ and R$_5$ each represent a hydrogen atom or R$_4$ and R$_5$ together represent an oxo group;

n stands for zero, 1 or 2, and pharmaceutically acceptable salts and individual optical isomers thereof.

16. A composition comprising an assayable amount of a compound of claim 1 in admixture or otherwise in association with an inert carrier.

17. A pharmaceutical composition comprising an effective immunosuppressive amount of a compound of claim 1 in admixture or otherwise in association with one or more pharmaceutically acceptable carriers or excipients.

18. A compound of claim 1 wherein the compound is 9-[(S)-(1-Oxo-2(R)-acetylthio-3-phenylpropyl)amino]-octahydro-10-oxo-6H-pyridazo[1,2-a][1,2]diazepine-1(S)-carboxylic acid.

19. A compound of claim 1 wherein the compound is 9-[(S)-(1-Oxo-2(R)-thio-3-phenylpropyl)amino]-octahydro-10-oxo-6H-pyridazo[1,2-a][1,2]diazepine-1(S)-carboxylic acid.

20. A compound of claim 1 wherein the compound is 9-[(S)-(1-Oxo-2(S)-acetylthio-3-phenylpropyl)amino]-octahydro-10-oxo-6H-pyridazo[1,2-a][1,2]diazepine-1(S)-carboxylic acid.

21. A compound of claim 1 wherein the compound is 9-[(S)-(1-Oxo-2(S)-thio-3-phenylpropyl)amino]-octahydro-10-oxo-6H-pyridazo[1,2-a][1,2]diazepine-1(S)-carboxylic acid.

22. A compound of claim 1 wherein the compound is 9-[(S)-(1-Oxo-2(S)-acetylthio-3-phenylpropyl)amino]-octahydro-10-oxo-6H-pyridazo[1,2-a][1,2]diazepine-1(S)-carboxylic acid, t-butyl ester.

23. A compound of claim 1 wherein the compound is 9-[(S)-(1-Oxo-2(S)-thio-3-phenylpropyl)amino]-octahydro-10-oxo- 6H-pyridazo[1,2-a][1,2]diazepine-1(S)-carboxylic acid, t-butyl ester.

24. A compound of claim 1 wherein the compound is [(S)-(1-Oxo-2(S)-acetylthio-3-phenylpropyl)amino]-octahydro-10-oxo-6H-pyridazo[1,2-a][1,2]diazepine-1(R)-carboxylic acid, t-butyl ester.

25. A compound of claim 1 wherein the compound is 9-[(S)-(1-Oxo-2(S)-thio-3-phenylpropyl)amino]-octahydro-10-oxo-6H-pyridazo[1,2-a][1,2]diazepine-1(R)-carboxylic acid, t-butyl ester.

26. A compound of claim 1 wherein the compound is 9-[(S)-(1-Oxo-2(S)-acetylthio-3-phenylpropyl)amino]-octahydro-10-oxo-6H-pyridazo[1,2-a][1,2]diazepine-1(R)-carboxylic acid.

27. A compound of claim i wherein the compound is 9-[(S)-(1-Oxo-2(S)-thio-3-phenylpropyl)amino]-octahydro-10-oxo-6H-pyridazo[1,2-a][1,2]diazepine-1(R)-carboxylic acid.

28. A compound of claim 1 wherein the compound is 9-((S)-(1-Oxo-2(S)-acetylthio-3-phenylpropyl)amino)-octahydro-6,10-dioxo-6H-pyridazo[1,2-a][1,2]diazepine-1(S)-carboxylic acid, t-butyl ester.

29. A compound of claim 1 wherein the compound is 9-((S)-(1-Oxo-2(S)-acetylthio-3-phenylpropyl)amino)-octahydro-6,10-dioxo-6H-pyridazo[1,2-a][1,2]diazepine-1(S)-carboxylic acid.

30. A compound of claim 1 wherein the compound is 9-((S)-(1-Oxo-2(S)-thio-3-phenylpropyl)amino)-octahydro-6,10-dioxo-6H-pyridazo[1,2-a][1,2]diazepine-1(S)-carboxylic acid.

31. A compound of claim 1 wherein the compound is 9-((S)-(1-Oxo-2(S)-thio-3-phenylpropyl)amino)-octahydro-6,10-dioxo-6H-pyridazo[1,2-a][1,2]diazepine-1(S)-carboxylic acid, t-butyl ester.

* * * * *

UNITED STATES PATENT AND TRADEMARK OFFICE
CERTIFICATE OF CORRECTION

PATENT NO. : 5,366,973          Page 1 of 7
DATED      : November 22, 1994
INVENTOR(S) : Gary A. Flynn, et al It is certified that error appears in the above-indentified patent and that said Letters Patent is hereby corrected as shown below:

Changing the title page, item [54] and column 1, lines 1-6, to read
--MERCAPTOACETYLAMIDO PYRIDAZO [1,2]PYRIDAZO[1,2]PYRIDAZINE, PYRAZOLO[1,2]PYRIDAZINE, PYRIDAZO[1,2-A][1,2]DIAZEPINE AND PYRAZOLOL[1,2-A][1,2] DIAZEPINE--.

Column 2, Line 50, patent reads: "natruiuretic" and should read -- natriuetic --.

Column 2, Line 57, patent reads: "naturiuretic" and should read -- natriuetic --.

Column 3, Line 54, patent reads: "i to 8" and should read -- 1 to 8 --.

Column 4, Line 20, patent reads: 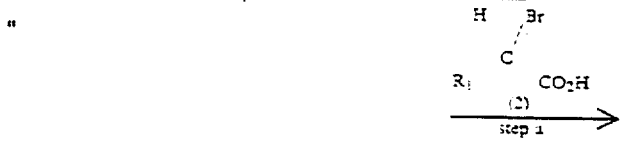 and should read -- 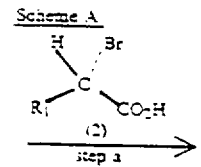

UNITED STATES PATENT AND TRADEMARK OFFICE
CERTIFICATE OF CORRECTION

PATENT NO. : 5,366,973  
DATED : November 22, 1994  
INVENTOR(S) : Gary A. Flynn, et al Page 2 of 7

It is certified that error appears in the above-indentified patent and that said Letters Patent is hereby corrected as shown below:

Column 5, Line 2, patent reads: "of structure converted" and should read -- of structure (3) is converted -- .

Column 5, Line 21, patent reads: " of of " and should read -- of -- .

Column 6, Line 7, patent reads: " (Sa) " and should read -- (8a) -- .

Column 6, Line 21, patent reads: " with the appropriate with chloromethyl" and should read -- with the appropriate chloromethyl --.

Column 6, Line 30, patent reads: " (Sa) " and should read -- (8a) -- .

Column 6, Line 35, patent reads: " with the appropriate with chloromethyl" and should read -- with the appropriate chloromethyl --.

Column 8, Line 35, patent reads: "51,03" and should read -- 51.03 --.

Column 8, Line 43, patent reads: "3phenyl" and should read -- 3-phenyl -- .

Colunm 12, Line 51, patent reads: "sustituting" and should read -- substituting -- .

Colunm 14, Line 50, patent reads: "sustituting" and should read -- substituting -- .

Column 15, Line 21, patent reads: " cm-11 " and should read -- cm-1 -- .

UNITED STATES PATENT AND TRADEMARK OFFICE
CERTIFICATE OF CORRECTION

PATENT NO. : 5,366,973  
DATED : November 22, 1994  
INVENTOR(S) : Gary A. Flynn, et al Page 3 of 7

It is certified that error appears in the above-indentified patent and that said Letters Patent is hereby corrected as shown below:

Column 15, Line 21, patent reads: " 7    8," and should read -- 7,8 -- .

Column 16, Line 41, patent reads: " 6,9dioxopyridazo " and should read -- 6,9-dioxopyridazo -- .

Column 16, Line 45, patent reads: " 6,9dioxopyridazo " and should read -- 6,9-dioxopyridazo -- .

Column 16, Line 48, patent reads: " 6,9dioxopyridazo " and should read -- 6,9-dioxopyridazo -- .

Column 17, Line 2, patent reads: " -9oxopyridazo " and should read -- -9-oxopyridazo -- .

Column 17, Line 5, patent reads: " -9oxopyridazo " and should read -- -9-oxopyridazo -- .

Column 17, Line 8, patent reads: " -9oxopyridazo " and should read -- -9-oxopyridazo -- .

Column 17, Line 11, patent reads: " -9oxopyridazo " and should read -- -9-oxopyridazo -- .

Column 17, Line 15, patent reads: " -9oxopyridazo " and should read -- -9-oxopyridazo -- .

Column 17, Line 19, patent reads: " -9oxopyridazo " and should read -- -9-oxopyridazo -- .

UNITED STATES PATENT AND TRADEMARK OFFICE
CERTIFICATE OF CORRECTION

PATENT NO. : 5,366,973
DATED : November 22, 1994
INVENTOR(S) : Gary A. Flynn, et al Page 4 of 7

It is certified that error appears in the above-indentified patent and that said Letters Patent is hereby corrected as shown below:

Column 18, Line 56, patent reads: " -9oxopyridazo " and should read -- -9-oxopyridazo -- .

Column 18, Line 59, patent reads: " -9oxopyridazo " and should read -- -9-oxopyridazo -- .

Column 18, Line 61, patent reads: " -9oxopyridazo " and should read -- -9-oxopyridazo -- .

Column 18, Line 66, patent reads: " -9oxopyridazo " and should read -- -9-oxopyridazo -- .

Column 19, Line 1, patent reads: " -9oxopyridazo " and should read -- -9-oxopyridazo -- .

Column 20, Line 51, patent reads: " 6,7    8," and should read -- 6,7,8 -- .

Column 20, Line 56, patent reads: " 6,7    8," and should read -- 6,7,8 -- .

Column 21, Line 14 & 15, patent reads: " 6,9diox-opyridazo " and should read -- 6,9-dixo-opyridazo -- .

Column 21, Line 18 & 19, patent reads: " 6,9diox-opyridazo " and should read -- 6,9-dixo-opyridazo -- .

Column 21, Line 21, patent reads: " 6,9diox-opyridazo " and should read -- 6,9-dixo-opyridazo -- .

Column 21, Line 22, patent reads: " pyridazine-i-carboxylic " and should read -- pyridazine-1-carboxylic -- .

Column 21, Line 24, patent reads: " 6,9dioxopyridazo " and should read -- 6,9-dioxopyridazo -- .

UNITED STATES PATENT AND TRADEMARK OFFICE
CERTIFICATE OF CORRECTION

PATENT NO. : 5,366,973  
DATED : November 22, 1994  
INVENTOR(S) : Gary A. Flynn, et al Page 5 of 7

It is certified that error appears in the above-indentified patent and that said Letters Patent is hereby corrected as shown below:

Column 21, Line 28, patent reads: " 6,9dioxopyridazo " and should read -- 6,9-dioxopyridazo -- .

Column 21, Line 31, patent reads: " 6,9dioxopyridazo " and should read -- 6,9-dioxopyridazo -- .

Column 21, Line 53, patent reads: " -9oxopyridazo " and should read -- -9-oxopyridazo -- .

Column 21, Line 56, patent reads: " -9oxopyridazo " and should read -- -9-oxopyridazo -- .

Column 21, Line 59, patent reads: " -9oxopyridazo " and should read -- -9-oxopyridazo -- .

Column 21, Line 62, patent reads: " -9oxopyridazo " and should read -- -9-oxopyridazo -- .

Column 21, Line 66, patent reads: " -9oxopyridazo " and should read -- -9-oxopyridazo -- .

Column 22, Line 1, patent reads: " -9oxopyridazo " and should read -- -9-oxopyridazo -- .

Column 22, Line 16 & 17, patent reads: " 6,9dioxopyridazo " and should read -- 6,9-dioxopyridazo -- .

Column 22, Line 19 & 20, patent reads: " 6,9dioxopyridazo " and should read -- 6,9-dioxopyridazo -- .

Column 23, Line 34, patent reads: " -9oxopyridazo " and should read -- -9-oxopyridazo -- .

UNITED STATES PATENT AND TRADEMARK OFFICE
CERTIFICATE OF CORRECTION

PATENT NO. : 5,366,973
DATED : November 22, 1994
INVENTOR(S) : Gary A. Flynn, et al It is certified that error appears in the above-indentified patent and that said Letters Patent is hereby corrected as shown below:

Column 23, Line 36, patent reads: " -9oxopyridazo " and should read -- -9-oxopyridazo -- .

Column 23, Line 40, patent reads: " -9oxopyridazo " and should read -- -9-oxopyridazo -- .

Column 23, Line 42, patent reads: " -9oxopyridazo " and should read -- -9-oxopyridazo -- .

Column 23, Line 46, patent reads: " -9oxopyridazo " and should read -- -9-oxopyridazo -- .

Column 23, Line 50, patent reads: " -9oxopyridazo " and should read -- -9-oxopyridazo -- .

Column 23, Line 67 continued on Column 24, Line 1, patent reads: " 6,9dioxopyridazo " and should read -- 6,9-dioxopyridazo -- .

Column 27, Line 55, patent reads: " 0,001% " and should read -- 0.001% -- .

Column 30, Line 45, patent reads: " gorup " and should read -- group --.

Column 31, Line 18, patent reads: " gorup " and should read -- group --.

Column 31, Line 66, patent reads: " gorup " and should read -- group --.

UNITED STATES PATENT AND TRADEMARK OFFICE
CERTIFICATE OF CORRECTION

PATENT NO. : 5,366,973
DATED : November 22, 1994
INVENTOR(S) : Gary A. Flynn, et al It is certified that error appears in the above-indentified patent and that said Letters Patent is hereby corrected as shown below:

Column 32, Line 40, patent reads: " gorup " and should read -- group --.

Column 33, Line 21 & 22, patent reads: " compound is [(S)- " and should read -- compound is 9-[(S)- --.

Column 34, Line 7, patent reads: " claim i" and should read -- claim 1 --.

Signed and Sealed this

Twenty-eighth Day of May, 1996

Attest:

BRUCE LEHMAN

*Attesting Officer*    *Commissioner of Patents and Trademarks*